(12) United States Patent
Tsumura et al.

(10) Patent No.: US 9,212,344 B2
(45) Date of Patent: Dec. 15, 2015

(54) CELL CULTURE DEVICE HAVING CULTURE MEDIUM REPLACEMENT FUNCTION

(71) Applicant: JTEC Corporation, Kobe-shi (JP)

(72) Inventors: Takashi Tsumura, Kobe (JP); Takahiro Ono, Kobe (JP)

(73) Assignee: JTEC CORPORATION, Kobe-shi (JP)

( * ) Notice: Subject to any disclaimer, the term of this patent is extended or adjusted under 35 U.S.C. 154(b) by 0 days.

(21) Appl. No.: 14/380,687

(22) PCT Filed: Feb. 28, 2013

(86) PCT No.: PCT/JP2013/055362
§ 371 (c)(1),
(2) Date: Aug. 22, 2014

(87) PCT Pub. No.: WO2013/129558
PCT Pub. Date: Sep. 6, 2013

(65) Prior Publication Data
US 2015/0010996 A1 Jan. 8, 2015

(30) Foreign Application Priority Data

Feb. 29, 2012 (JP) .................................. 2012-043034

(51) Int. Cl.
| | |
|---|---|
| *C12M 3/00* | (2006.01) |
| *C12M 1/00* | (2006.01) |
| *C12M 1/12* | (2006.01) |
| *C12M 1/36* | (2006.01) |
| *C12M 1/26* | (2006.01) |

(52) U.S. Cl.
CPC ............... *C12M 25/06* (2013.01); *C12M 29/00* (2013.01); *C12M 29/10* (2013.01); *C12M 33/04* (2013.01); *C12M 41/14* (2013.01); *C12M 41/48* (2013.01)

(58) Field of Classification Search
CPC ...... C12M 41/12; C12M 41/14; C12M 25/00; C12M 23/48
See application file for complete search history.

(56) References Cited

U.S. PATENT DOCUMENTS 3,844,896 A * 10/1974 Sharpe ........................ 435/286.4
4,170,861 A * 10/1979 Snyder et al. .................... 53/468
(Continued)

FOREIGN PATENT DOCUMENTS

| JP | S52-134081 | 11/1977 |
|---|---|---|
| JP | 58-155082 A | 9/1983 |

(Continued)

OTHER PUBLICATIONS

Written Opinion for International Application No. PCT/JP2013/055362 dated Apr. 16, 2013.

*Primary Examiner* — Nathan Bowers
(74) *Attorney, Agent, or Firm* — Kratz, Quintos & Hanson, LLP

(57) ABSTRACT

Provided is a small-scale cell culture apparatus having a culture medium replacement function for culturing cells in a small number of Petri dishes, the cell culture apparatus being capable of performing automatic replacement of the culture medium and cell culture within the same cavity and significantly reducing the apparatus cost. At least one set of upper and lower discs is arranged inside an incubator chamber 1. Petri dishes 4, 6 in each of which cells and a culture medium are put are held on lower discs 18, 19, and top lids 5, 7 are held on upper discs 19, 30. The lower side of each of the top lids is open.

11 Claims, 27 Drawing Sheets

(56) References Cited

U.S. PATENT DOCUMENTS

| | | | |
|---|---|---|---|
| 4,468,914 A * | 9/1984 | Pestes | 53/505 |
| 4,515,286 A * | 5/1985 | Ushikubo | 220/314 |
| 5,271,897 A * | 12/1993 | Wurschum et al. | 422/63 |
| 6,129,428 A * | 10/2000 | Helwig et al. | 312/114 |
| 6,228,636 B1 * | 5/2001 | Yahiro et al. | 435/303.1 |
| 6,673,595 B2 * | 1/2004 | Barbera-Guillem | 435/286.2 |
| 2003/0031602 A1 * | 2/2003 | Weselak et al. | 422/104 |
| 2008/0063573 A1 * | 3/2008 | Ammann et al. | 422/105 |
| 2012/0125483 A1 * | 5/2012 | Brelivet | 141/369 |

FOREIGN PATENT DOCUMENTS

| | | |
|---|---|---|
| JP | 2003-245065 A | 9/2003 |
| JP | 2006-014675 A | 1/2006 |
| JP | 2006-115798 A | 5/2006 |
| JP | 2006-141328 A | 6/2006 |
| JP | 2006-149268 A | 6/2006 |
| JP | 2010-268813 A | 12/2010 |

* cited by examiner

CELL CULTURE DEVICE HAVING CULTURE MEDIUM REPLACEMENT FUNCTION

TECHNICAL FIELD

The present invention relates to a cell culture device having a culture medium replacement function, and more specifically to a cell culture device having a culture medium replacement function for culturing cells or fungi in a Petri dish.

BACKGROUND ART

Conventionally, cells have been cultured by repeatedly performing the following operation. A culture medium and cells are put in a Petri dish, the Petri dish is housed inside an incubator in which environment such as temperature and atmospheric gas is controlled with a top lid closed to thereby culture the cells, the Petri dish is taken out of the incubator at every predetermined period and transferred to an operation space in which dispensation and separation are performed, the culture medium is replaced in the operation space, and the Petri dish is again returned to the incubator. When a culture medium replacement operation is manually performed, it is necessary not only to pay careful attention to prevent various germs and contamination from being mixed therein during the operation, but also to perform the culture medium replacement in every two or three days. Further, the replacement time may be midnight. Therefore, researchers and operators have been forced to bear heavy labor and burden. In view of the above, in recent years, there has been provided an automatic cell culture apparatus capable of automatically replacing a culture medium.

Patent Document 1 discloses a cell culture apparatus in which a culture cassette with a Petri dish housed and held therein is freely detachably placed inside an incubator and a gas pipe for introducing and discharging gas is detachably connected to the culture cassette having a sealed structure to thereby perform cell culture while controlling the temperature, gas, and the like. The incubator is provided with an opening/closing door which can be automatically opened and closed. The opening/closing door is opened, and the culture cassette is taken out and transferred to an operation room using a robot hand. Thereafter, a lid body of the culture cassette is opened, and the Petri dish is taken out using another robot hand and set at a predetermined position in the operation room. After performing treatment such as a fractionating/dispensing operation for replacing the culture medium and an inspection operation, the Petri dish set in the operation room is housed in the culture cassette in the reverse procedure of the above procedure, and the culture cassette is then returned to the incubator. In the fractionating/dispensing operation in the operation room, a top lid of the Petri dish is detached using a robot hand, and the main body of the Petri dish is inclined inside the operation room to collect the old culture medium in one side. Liquid of the collected old culture medium is sucked out using a suction tool, a new culture medium is then filled in the Petri dish, and the top lid is then attached thereto.

Patent Document 2 discloses an automatic cell culture apparatus that is provided with an operation unit for performing a culture operation necessary for culturing cells of subjects, incubator units for culturing the cells, storage units for storing reagents necessary for culture and culture tools, a steam supply unit for performing autoclave sterilization, and an inlet-outlet unit for taking in and out reagents and culture tools. The incubator unite, the storage units, and the inlet-outlet unit communicate with the operation unit, and have sealing doors leading to the operation unit. By selecting and opening/closing the sealing doors, sterilizing steam from the seam supply unit is supplied to the operation unit, and any of the incubator units, the storage units, and the inlet-outlet unit communicating with the operation unit.

The operation unit is provided with an operation robot, a centrifugal separator, and a culture operation unit which is necessary for culturing cells. The culture operation unit includes a turntable, a pipetting device, and a centrifugal tube handling device. The culture operation necessary for culturing cells includes a culture medium replacement operation and a subculture operation. As also described in Patent Document 3, a general-purpose multijoint industrial robot is used as the operation robot that carries out an actual culture operation on behalf of human resources. A multijoint industrial robot can perform substantially the same operation as manual operation by controlling the robot by a computer. Further, a multijoint industrial robot can also perform different operations by rewriting a control program and therefore has versatility. However, because a multijoint industrial robot is extremely expensive, an automatic cell culture apparatus is also a large-scale and expensive system and therefore cannot be easily utilized.

CITATION LIST

Patent Literatures

Patent Document 1: JP-A No. 2006-014675
Patent Document 2: JP-A No. 2006-115798
Patent Document 3: JP-A No. 2006-149268

SUMMARY OF INVENTION

Technical Problem

In view of the above situation, a problem to be solved by the present invention is to provide a small-scale cell culture apparatus having a culture medium replacement function for culturing cells in a small number of Petri dishes, the cell culture apparatus being capable of performing automatic replacement of the culture medium and cell culture within the same cavity and significantly reducing the apparatus cost.

Solution to Problem

In order to solve the above problem, the present invention has configured a cell culture apparatus having a culture medium replacement function, wherein at least one set of upper and lower discs each fixed to a rotatable shaft is horizontally arranged inside an incubator chamber, Petri dishes in each of which cells and a culture medium are put are held on the lower disc, top lids are held on the upper disc, a lower side of each of the top lids is open, it is possible to achieve a state in which the lower disc and the upper disc are brought vertically close to each other to cover the Petri dishes with the top lids and a state in which the lower disc and the upper disc are vertically separated from each other and one of the lower disc and the upper disc is rotated by a predetermined angle to laterally shift the top lids from the Petri dishes so that the Petri dishes are partially exposed, culture medium replacement means is inserted into the exposed portion of a Petri dish from the upper side through an insertion hole formed on the upper disc and the culture medium is replaced, the culture medium replacement means is then retracted, and the lower disc and the upper disc are rotated and vertically displaced to cover the Petri dishes with the top lids to continue cell culture.

More specifically, the cell culture apparatus having a culture medium replacement function of the present invention has a configuration in which an incubator chamber and a drive chamber located above the incubator chamber are arranged with a partition wall interposed therebetween, a rotary shaft body includes a first shaft body and a second shaft body which both have the same rotation center and are coaxially arranged wherein the first shaft body is slidable in the axial direction relative to the second shaft body and the first shaft body and the second shaft body are relatively rotatable by a predetermined angle, the rotary shaft body being allowed to vertically pass through a shaft hole formed on the partition wall and supported by a bearing unit, the second shaft body of the rotary shaft body is supported so as to be rotatable at a fixed position and driven to rotate by a motor arranged inside the drive chamber, and the first shaft body of the rotary shaft body is driven to move up and down in the vertical direction by a linear actuator arranged inside the drive chamber, a lower disc which holds Petri dishes is directly or indirectly concentrically fixed to a lower part of the second shaft body and an upper disc which holds top lids of the Petri dishes is directly or indirectly concentrically fixed to a lower part of the first shaft body inside the incubator chamber, a plurality of holding units which mount thereon and hold the Petri dishes are provided in the lower disc on the same circumference at every constant rotation angle, a plurality of openings which receive the Petri dishes are formed on the upper disc so that the center of each of the openings is located at the same position as the center of the corresponding holding unit, top lid holding units which hold outer peripheral parts of the top lids of the Petri dishes are provided on peripheral edges of the openings, and insertion holes are formed to penetrate the upper disc at positions close to one side of top lids held on the top lid holding units, a suction tube and an ejection tube for sucking and ejecting a culture medium and constituting the culture medium replacement means are allowed to penetrate the partition wall so as to hang down to the incubator chamber and driven to move up and down by a linear actuator provided inside the drive chamber, and cells are cultured in a state in which the upper disc is moved down with the relative rotation angle between the upper disc and the lower disc maintained zero to cover the Petri dishes with the top lids, the upper disc is then moved up and the lower disc is rotationally displaced by a predetermined angle relative to the upper disc to shift the top lids from the Petri dishes, the suction tube and the ejection tube are moved down so that tips of the suction tube and the ejection tube are located inside a Petri dish through the corresponding insertion hole of the upper disc, an old culture medium is discharged using the suction tube, and a new culture medium is then injected from the ejection tube to automatically replace the culture medium.

Further, the cell culture apparatus of the present invention is preferably configured in such a manner that two or more sets, each of the sets including a lower disc which holds Petri dishes and an upper disc which holds top lids of the Petri dishes, are vertically arranged in multiple stages, a lower disc on each of the stages is directly or indirectly fixed to the lower part of the second shaft body, an upper disc on each of the stages is directly or indirectly fixed to the lower part of the first shaft body, all lower discs on the respective stages are integrally driven to rotate by the second shaft body, all upper discs on the respective stages are integrally driven to move up and down by the first shaft body, Petri dishes and top lids held on the respective stages are held at positions displaced by a predetermined angle in one rotation direction from the highest stage to the lowest stage so that all the Petri dishes are set to be partially exposed in plan view when shifting the top lids therefrom, the insertion holes are formed on the upper disc on each of the stages at positions corresponding to the exposed portions of the Petri dishes located below, through holes are formed on at least lower discs on the respective stages excepting the lowest stage at positions corresponding to the exposed portions of Petri dishes located on the lower stage, the culture medium replacement means is inserted into a Petri dish on the highest stage through the corresponding insertion hole of the upper disc on the highest stage to replace the culture medium, and the culture medium replacement means is inserted into a Petri dish on each of the other lower stages through the insertion holes of the respective upper discs and the through holes of the respective lower discs located thereabove to replace the culture medium.

Further, the cell culture apparatus of the present invention preferably includes synchronous rotation means which functions in a state in which the upper disc is moved down with the relative rotation angle between the upper disc and the lower disc maintained zero to cover Petri dishes with top lids and integrates the upper disc and the lower disc with each other with respect to rotation and rotation restriction means which functions in a state in which the upper disc is moved upward to remove top lids from Petri dishes and prevents rotation of the upper disc.

Further, in the present invention, a lower part of the rotary shaft body located inside the incubator chamber includes a cylindrical outer shaft portion composed of one of the first shaft body and the second shaft body and an inner shaft portion located inside the outer shaft portion and composed of the other one of the first shaft body and the second shaft body, one of the upper disc and the lower disc is fixed to a plurality of fixation pieces which are provided in a projecting manner on the outer periphery of the outer shaft portion, the other one of the upper disc and the lower disc is fixed to a plurality of fixation pieces which are provided in a projecting manner on the outer periphery of the inner shaft portion and project outward in the radial direction through a plurality of opening portions formed on the outer shaft portion, and the opening portions have a size that allows the fixation pieces of the inner shaft portion to relatively move upward and displace by a predetermined angle inside thereof at the time of an operation for opening the top lids.

Further, in the present invention, the rotary shaft body located inside the incubator chamber includes a connection unit which is located above the upper disc on the highest stage and capable of vertically separating and connecting the first shaft body and the second shaft body.

Further, in the present invention, a through hole through which the suction tube and the ejection tube are introduced into the incubator chamber is formed on the partition wall, a support rod which is driven to move up and down by a linear actuator provided in the drive chamber is vertically arranged so as to pass through the through hole, the suction tube and the ejection tube is allowed to penetrate a flange plate which is fixed to a lower end of the support rod and located inside the incubator chamber and fixed thereto, the through hole is airtightly closed by the flange plate when the support rod is moved upward, and the support rod is moved downward to introduce the tips of the suction tube and the ejection tube into the Petri dish.

Further, in the present invention, the bearing unit which rotatably supports the rotary shaft body on the partition wall and the rotary shaft body each include a gas seal function for maintaining the incubator chamber in an air-tight state.

Further, in the present invention, an opening/closing door is provided on the front of the incubator chamber, cutout portions are formed so that, when the positions of the holding units of the lower disc and the positions of the top lid holding units of the upper disc are vertically aligned to each other, fingers can pass from the outer peripheral parts through the holding units and the top lid holding units, and the cutout portions of the upper disc are allowed to communicate with the openings.

Further, each of the holding units of the lower disc is a recessed step portion which is formed on the upper face of a surrounding area of the corresponding cutout portion and receives a bottom part of a Petri dish.

Further, each of the top lid holding units of the upper disc abuttingly locks the outer peripheral face of a top lid of a Petri dish and includes three or more locking claws which support the lower edge of the top lid and are arranged on a peripheral edge part of the corresponding opening.

Advantageous Effects of Invention

In the above cell culture apparatus having a culture medium replacement function of the prevent invention, Petri dishes are held by the holding units of the lower disc inside the incubator chamber, and top lids are held by the top lid holding units of the upper disc. By first putting cells and a culture medium in each of the Petri dishes and setting the Petri dishes, the cells can be cultured thereafter while automatically replacing the cell culture medium. That is, it is possible to, automatically, shift the top lids from the Petri dishes, discharge an old culture medium using the suction tube, inject a new culture medium using the ejection tube, cover the Petri dishes with the top lids, and continue the cell culture. These operations can be performed inside the incubator chamber. Therefore, the apparatus is downsized and the structure is simplified. As a result, it is possible to significantly reduce the apparatus cost, and reduce the burden on researchers and operators.

Further, when a plurality of sets of lower discs which hold Petri dishes and upper discs which hold top lids of the Petri dishes are provided in multiple stages, a relatively large number of Petri dishes can be set at the same time and cells can be efficiently cultured even in a small-scale cell culture apparatus. Further, it is possible to automatically replace the culture medium in each of the Petri dishes individually, and improve the flexibility on the design. Therefore, the number of Petri dishes to be held on each stage and the number of stages can be optimally set depending on the size of each Petri dish and the area of a space of the incubator chamber. As a result, it is possible to provide the cell culture apparatus having high space efficiency.

Further, the synchronous rotation means which functions in a state in which Petri dishes are covered with top lids and integrates the upper disc and the lower disc with each other with respect to rotation and the rotation restriction means which functions in a state in which the upper disc is moved upward to remove top lids from Petri dishes and prevents rotation of the upper disc are provided. Therefore, it is possible to achieve basic functions of the present invention such as an opening/closing operation of the top lids and setting of the positions of the Petri dishes with respect to the culture medium replacement function by using a simple structure in which the upper disc is driven to move up and down in the vertical direction by the linear actuator and free to rotation, and only the lower disc is driven to rotate by the motor.

Further, when the rotary shaft body located inside the incubator chamber includes the connection unit which is located above the upper disc on the highest stage and capable of vertically separating and connecting the first shaft body and the second shaft body, it is possible to take the lower disc which holds the Petri dishes and the upper disc which holds the top lids out of the incubator chamber together with the lower part of the rotary shaft body, and perform advanced cleaning and sterilization treatment thereon.

Further, the bearing unit which rotatably supports the rotary shaft body on the partition wall and the rotary shaft body each include a gas seal function for maintaining the incubator chamber in an air-tight state. Therefore, when performing various disinfection/sterilization treatments such as autoclave and ozone sterilization, it is possible to maintain the incubator chamber in an air-tight state, protect the drive units placed inside the drive camber such as the motor and the linear actuator from various gases such as high temperature/high pressure steam and ozone, and prevent the entrance of various germs and contamination from the drive chamber during performing cell culture.

Further, the opening/closing door is provided on the front of the incubator chamber, the cutout portions are formed so that, when the positions of the holding units of the lower disc and the positions of the top lid holding units of the upper disc are vertically aligned to each other, fingers can pass from the outer peripheral parts through the holding units and the top lid holding units, and the cutout portions of the upper disc are allowed to communicate with the openings. Accordingly, when cells and a culture medium are first put into a Petri dish and the Petri dish is covered with a top lid, the opening/closing door is then opened, and the Petri dish and the top lid are pinched with fingers and set on the disc, the fingers can be allowed to advance in the center direction of the disc by virtue of the cutout portions of the lower disc and the upper disc. Then, by dropping the Petri dish through the opening of the upper disc, the Petri dish is held by the holding unit of the lower disc and, at the same time, the top lid is held by the top lid holding unit of the upper disc. Therefore, an operation for setting the Petri dish is made extremely easy.

BRIEF DESCRIPTION OF THE DRAWINGS

FIG. 13 is a partial cross-sectional view of a main part in a state in which the top lids are laterally shifted from the Petri dishes held on the holder so as to partially open the Petri dishes.

FIG. 23 is a partially-exploded perspective view illustrating the structure of the lower part of the rotary shaft body.

DESCRIPTION OF EMBODIMENTS

Figure 1:
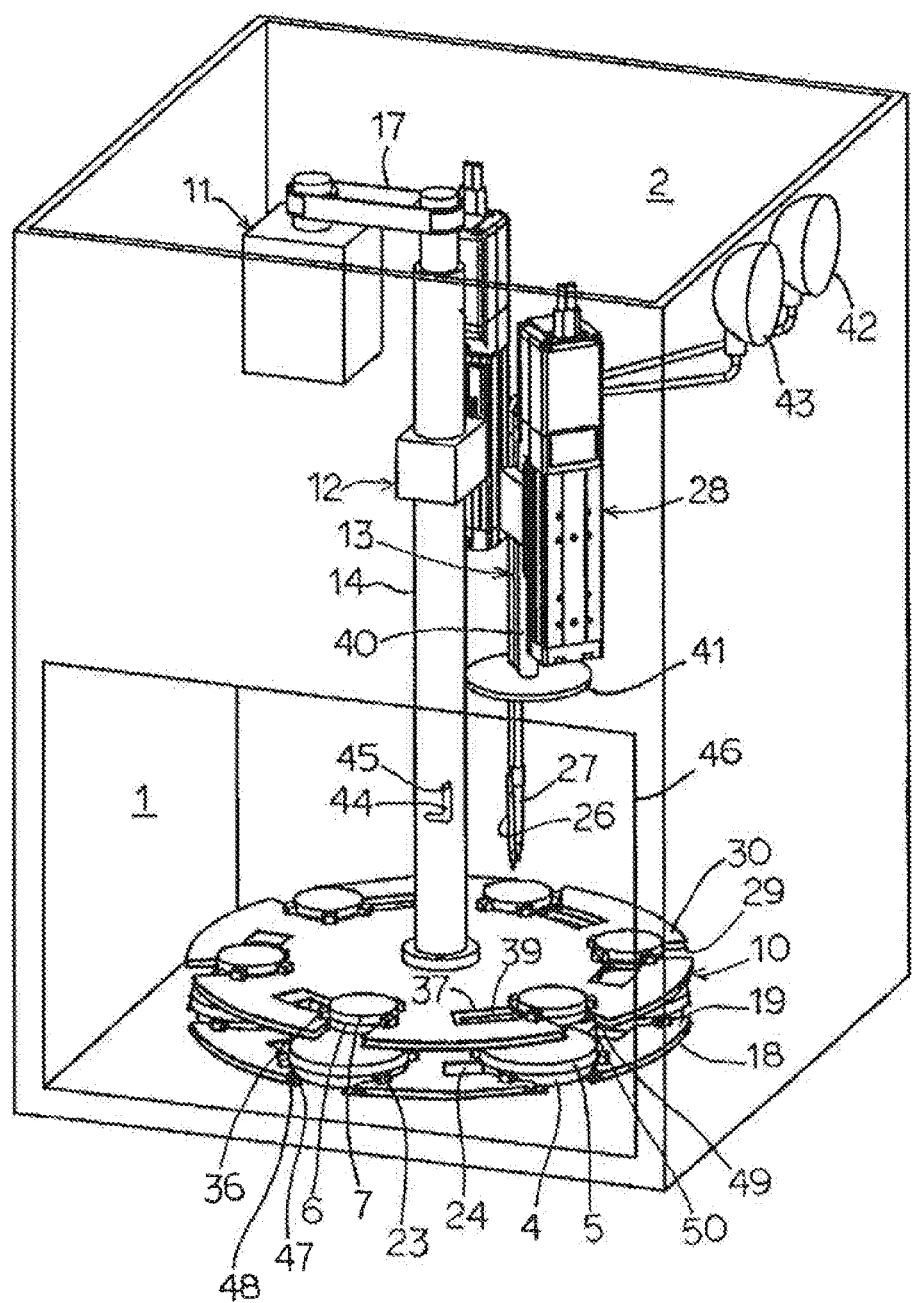
FIG. 1 is a partially-omitted entire perspective view illustrating a cell culture apparatus having a culture medium replacement function according to a first embodiment of the present invention by seeing through the internal structure of the cell culture apparatus.
Figure 2:
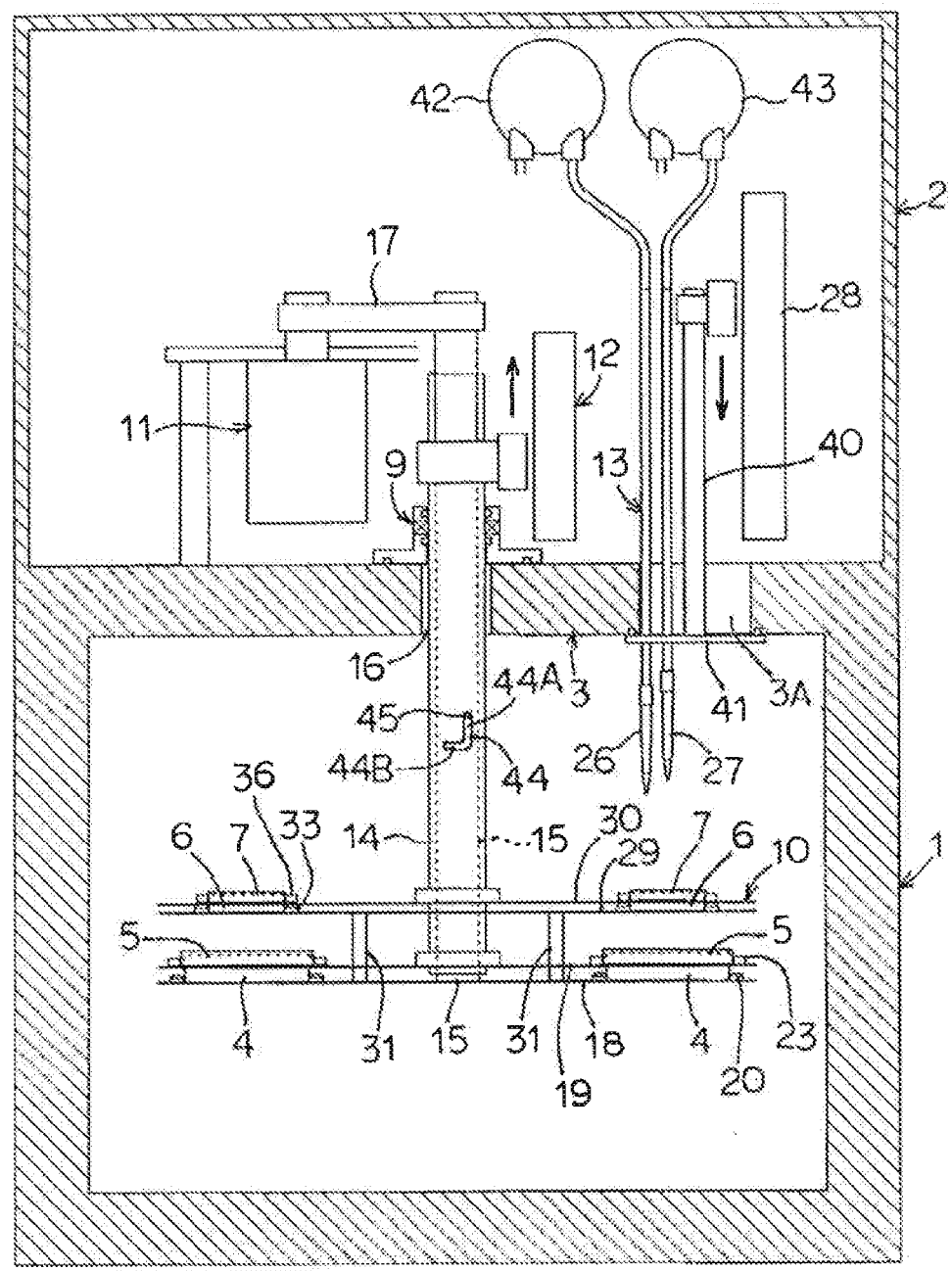
FIG. 2 is a partially-omitted longitudinal sectional view of the cell culture apparatus of the first embodiment.

Next, the present invention will be described in more detail on the basis of embodiments illustrated in the accompanying drawings. FIGS. 1 and 2 illustrate a cell culture apparatus having a culture medium replacement function according to a first embodiment of the present invention. FIGS. 3 to 6 illustrate discs which constitute a holder for holding Petri dishes and top lids. In the drawings, reference numeral 1 denotes an incubator chamber, 2 denotes a drive chamber, 3 denotes a partition wall, 4 denotes a Petri dish, 5 denotes a top lid, 6 denotes an upper Petri dish, 7 denotes a top lid, 8 denotes a rotary shaft body, 9 denotes a bearing unit, 10 denotes a holder, 11 denotes a drive motor, 12 denotes a linear actuator, and 13 denotes culture medium replacement means.

In the present invention, as illustrated in FIGS. 1 and 2, the incubator chamber 1 and the drive chamber 2 located above the incubator chamber 1 are arranged with the partition wall 3 interposed therebetween. The rotary shaft body 8 is vertically arranged so as to penetrate the partition wall 3, and supported by the bearing unit 9 so as to be slidable in the axial direction as well as rotatable. The holder 10 is provided on the lower end part of the rotary shaft body 8 inside the incubator chamber 1. Further, the upper part of the rotary shaft body 8 is driven to rotate by the drive motor 11 inside the drive chamber 2. The holder 10 can hold a plurality of Petri dishes 4 and a plurality of top lids 5 thereof, and a plurality of upper Petri dishes 6 and a plurality of top lids 7 thereof. The culture medium replacement means 13 is provided so as to penetrate the partition wall 3. The top lids 5 can be laterally shifted from the Petri dishes 4 and the top lids 7 can be laterally shifted from the upper Petri dishes 6 with the top lids 5, the Petri dishes 4, the top lids 7, and the upper Petri dishes 6 held by the holder 10 inside the incubator chamber 1 so that the culture medium can be automatically replaced.

The rotary shaft body 8 includes a first shaft body 14 and a second shaft body 15 which both have the same rotation center and are coaxially arranged. The first shaft body 14 is slidable in the axial direction relative to the second shaft body 15, and the first shaft body 14 and the second shaft body 15 are relatively rotatable to each other by a predetermined angle. The second shaft body 15 of the rotary shaft body 8 is supported so as to be rotatable at a fixed position and driven to rotate by the drive motor 11 which is arranged inside the drive chamber 2. The first shaft body 14 of the rotary shaft body 8 is driven to move up and down in the vertical direction by the linear actuator 12 which is arranged inside the drive chamber 2. In the present embodiment, the first shaft body 14 is a rotary cylinder having a cylindrical shape and the second shaft body 15 is a center shaft located inside the first shaft body 14. Therefore, in the following first embodiment, the first shaft body 14 is denoted by the rotary cylinder 14, and the second shaft body 15 is denoted by the center shaft 15.

More specifically, in the rotary shaft body 8, the center shaft 15 is allowed to coaxially pass through the inside of the rotary cylinder 14. Further, the rotary cylinder 14 is slidable in the axial direction relative to the center shaft 15, and the center shaft 15 is rotationally displaceable by a predetermined angle relative to the rotary cylinder 14. The rotary shaft body 8 is vertically arranged so as to pass through a shaft hole 16 which is formed on the partition wall 3. The center shaft 15 of the rotary shaft body 8 is supported so as to be rotatable at a fixed position inside the drive chamber 2. The rotary cylinder 14 is supported by the bearing unit 9 so as to be slidable in the axial direction as well as rotatable inside the drive chamber 2. The upper end part of the center shaft 15 is supported by a thrust and radial bearing (not illustrated) so as to be rotatable at a fixed position inside the drive chamber 2 to support the load of the rotary shaft body 8 and the holder 10. The bearing unit 9 has a braking function (rotation restriction means) with respect to the movement of the rotary cylinder 14 and a seal function for maintaining an air-tight state. For example, seal units each of which is composed of an O-ring are provided in upper and lower parts of the bearing, and the braking function and the seal function are achieved by the O-rings. The center shaft 15 is driven to rotate by the drive motor 11, a toothed pulley, and a timing belt 17. The rotary cylinder 14 is driven to move up and down in the vertical direction by the linear actuator 12. The drive motor 11 can accurately adjust the rotation angle of the center shaft 15 to rotate the center shaft 15, and a stepping motor or a servo motor is used as the drive motor 11.

Figure 3:
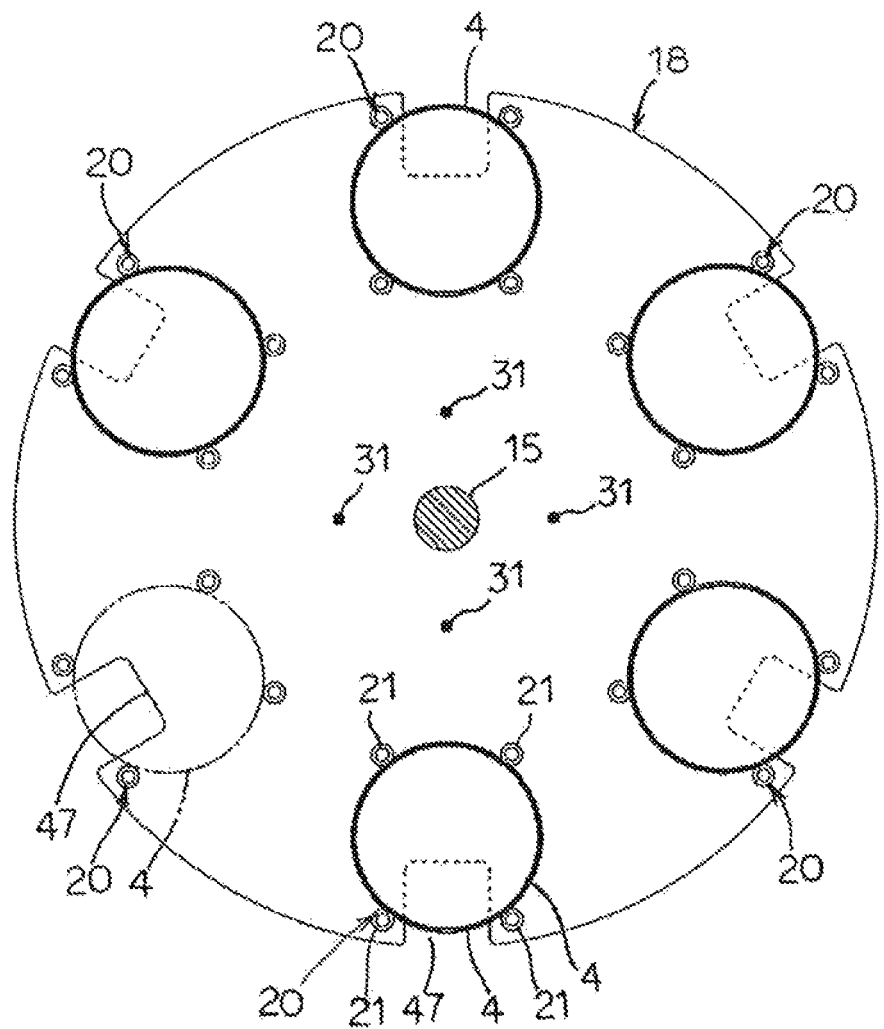
FIG. 3 is a plan view illustrating a state in which Petri dishes are held on a lower-stage lower disc.
Figure 4:
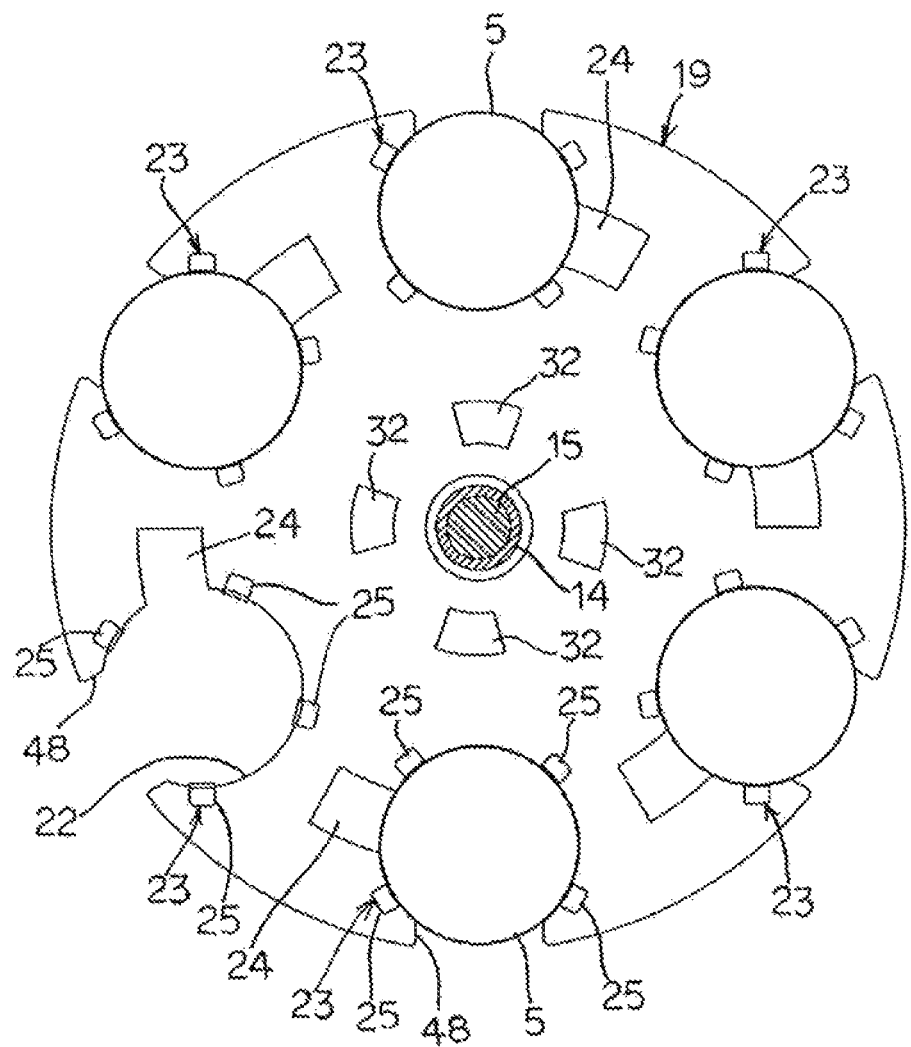
FIG. 4 is a plan view illustrating a state in which top lids of the Petri dishes are held on a lower-stage upper disc.
Figure 5:
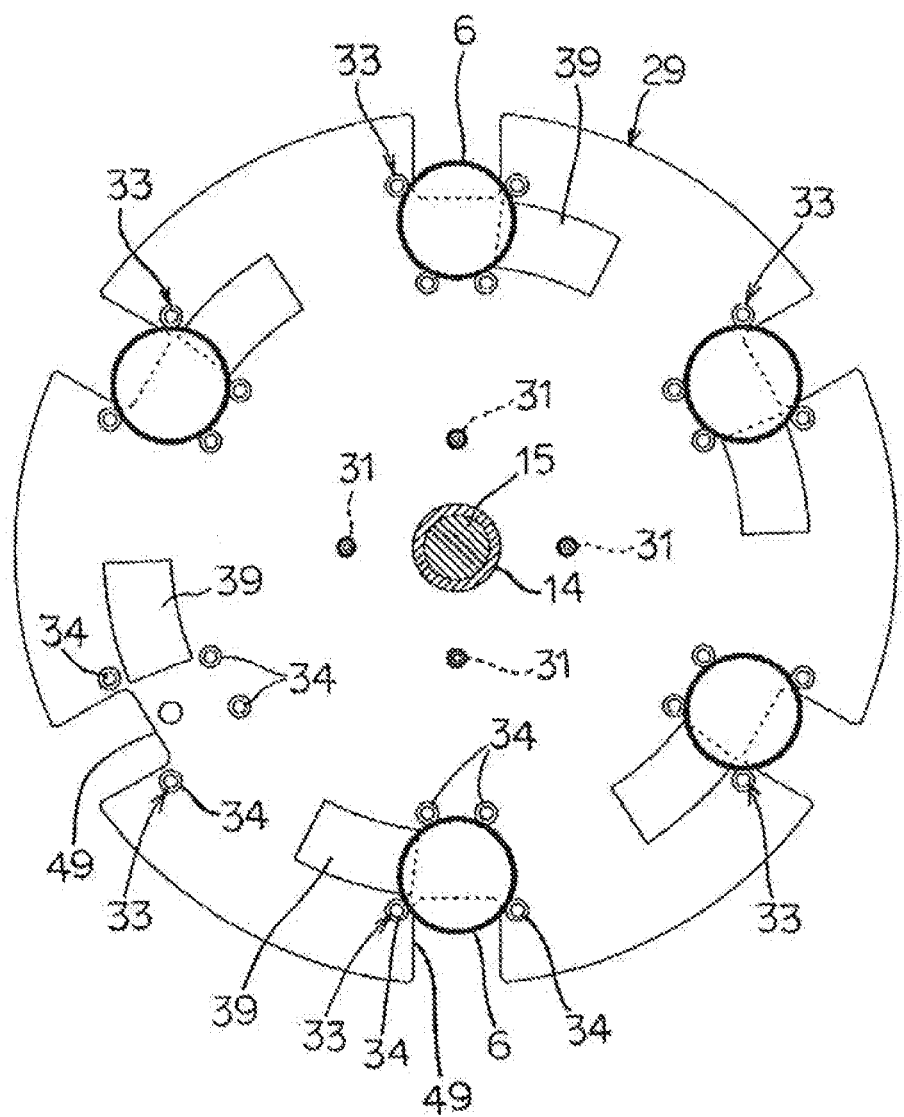
FIG. 5 is a plan view illustrating a state in which upper Petri dishes are held on an upper-stage lower disc.

The holder 10 is configured in such a manner that the center of a lower disc 18 which holds the Petri dishes 4 is fixed to the lower end of the center shaft 15, and the center of an upper disc 19 which holds the top lids 5 of the Petri dishes 4 is fixed to the lower end of the rotary cylinder 14. As illustrated in FIG. 3, in the lower disc 18, a plurality of holding units 20 which mount thereon and hold the Petri dishes 4 are provided on the same circumference at every constant rotation angle. Specifically, each of the holding units 20 of the lower disc 18 includes three or more projections 21 which abuttingly lock the outer peripheral face of the Petri dish 4. In the present embodiment, four projections 21 are provided on the upper face of the lower disc 18 so as to surround the Petri dish 4. As illustrated in FIG. 4, openings 22 which receive the Petri dishes 4 are formed on the upper disc 19 so that the center of each of the openings 22 is located at same position as the center of the corresponding holding unit 20. Top lid holding units 23 which hold the outer peripheral parts of the top lids 5 of the Petri dishes 4 are provided on the peripheral edge parts of the respective openings 22. Further, insertion holes 24 are formed to penetrate the upper disc 19 at positions close to one side of the top lids 5 held by the top lid holding units 23. Specifically, each of the top lid holding units 23 of the upper disc 19 abuttingly locks the top lid 5 of the Petri dish 4, and includes three or more locking claws 25 which support the lower edge of the top lid 5 and are arranged on the peripheral edge part of the opening 22. In the present embodiment, four locking claws 25 are provided in a projecting manner on the upper face of the upper disc 19 so as to surround the top lid 5 on the peripheral edge part of the opening 22. In the present embodiment, six Petri dishes 4 and six top lids 5 can be set.

A suction tube 26 and an ejection tube 27 which constitute the culture medium replacement means 13 are allowed to penetrate the partition wall 3 so as to hang down to the incubator chamber 1, and driven to move up and down by a linear actuator 28 which is provided inside the drive chamber 2. Cells are cultured in a state in which the upper disc 19 is moved down with the relative rotation angle between the upper disc 19 and the lower disc 18 maintained zero to thereby cover the Petri dishes 4 with the top lids 5. Thereafter, the upper disc 19 is moved up, and the lower disc 18 is rotationally displaced by a predetermined angle relative to the upper disc 19 to thereby shift the top lids 5 from the Petri dishes 4. In this state, the suction tube 26 and the ejection tube 27 are moved down so that the tips thereof are located inside the Petri dish 4 through the insertion hole 24 of the upper disc 19. An old culture medium is discharged using the suction tube 26, and a new culture medium is then injected from the ejection tube 27 to thereby automatically replace the culture medium. In this case, the tip of the ejection tube 27 is set at a position that is slightly higher than the tip of the suction tube 26 so as to prevent the tip of the ejection tube 27 from making contact with an old culture medium when the old culture medium is sucked using the suction tube 26.

In the present embodiment, two sets of discs, each of the sets including two discs, are horizontally arranged up and down. A set of discs on the lower stage includes the lower disc 18 and the upper disc 19 described above. The lower disc 18 and the upper disc 19 are respectively referred to as a lower-stage lower disc 18 and a lower-stage upper disc 19. A set of discs on the upper stage includes an upper-stage lower disc 29 and an upper-stage upper disc 30. The center of the upper-stage lower disc 29 is loosely fitted with the rotary cylinder 14 and fixed to the center shaft 15. The center of the upper-stage upper disc 30 is fixed to the rotary cylinder 14. The upper-stage lower disc 29 is connected to and integrated with a plurality of connection rods 31 which are provided in a standing manner in the lower-stage lower disc 18 on the central side with respect to the holding units 20. A plurality of escape holes 32 through which the connection rods 31 are inserted are formed on the lower-stage upper disc 19, and the escape holes 32 allow relative displacement of the connection rods 31.

Figure 6:
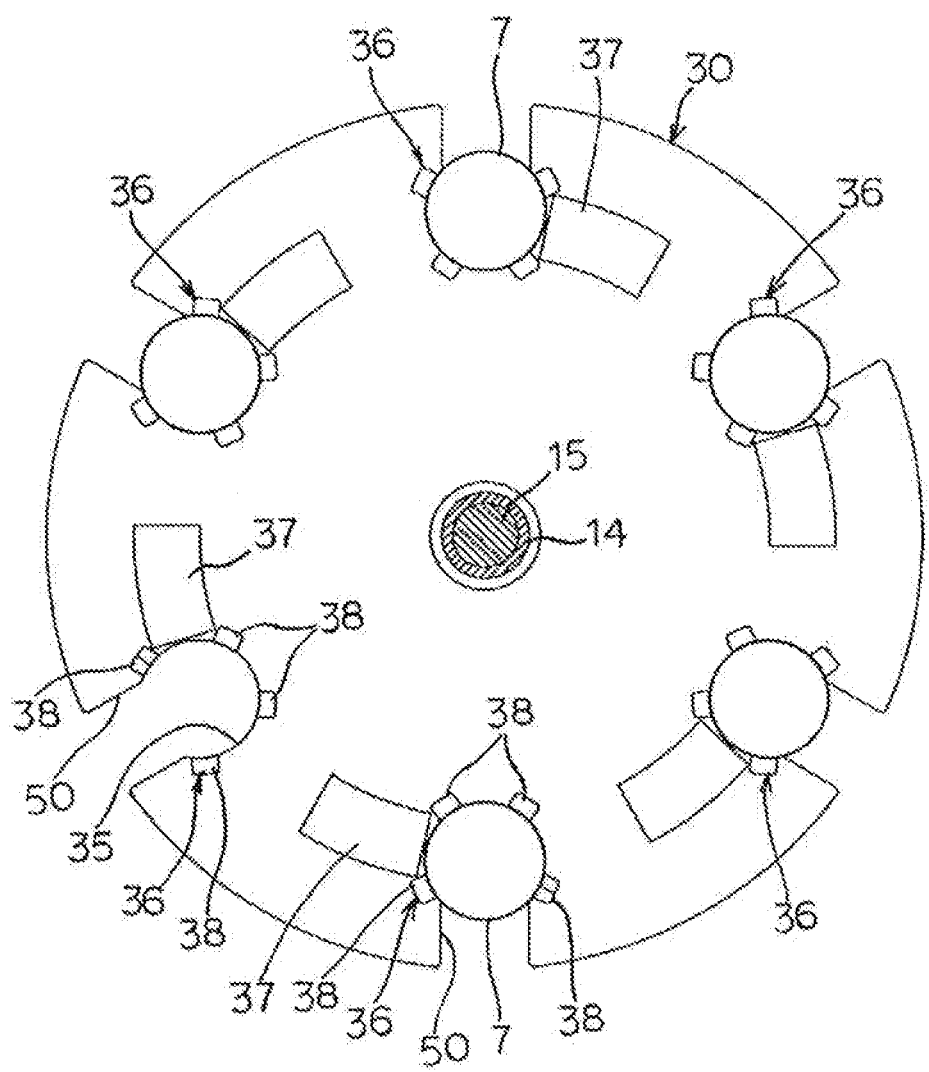
FIG. 6 is a plan view illustrating a state in which top lids of the upper Petri dishes are held on an upper-stage upper disc.

In the same manner as described above, as illustrated in FIG. 5, a plurality of second holding units 33 are provided in the upper-stage lower disc 29 at positions corresponding to the holding units 20 of the lower-stage lower disc 18, and upper Petri dishes 6 smaller than the Petri dishes 4 are mounted on and held by the second holding units 33. Each of the second holding units 33 includes four projections 34 which abuttingly lock the outer peripheral face of the upper Petri dish 6. Apart of each of the Petri dish 4 is vertically exposed on the lateral side of the corresponding upper Petri dish 6. As illustrated in FIG. 6, openings 35 which receive the upper Petri dishes 6 are formed on the upper-stage upper disc 30 so that the center of each of the openings 35 is located at same position as the center of the corresponding holding unit 20. Top lid holding units 36 which hold the outer peripheral parts of the top lids 7 of the upper Petri dishes 6 are provided on the peripheral edge parts of the respective openings 35. Further, insertion holes 37 are formed to penetrate the upper-stage upper disc 30 at positions close to one side of the top lids 7 held by the top lid holding units 36. In the same manner as described above, each of the top lid holding units 36 includes four locking claws 38.

Further, through holes 39 are formed on the upper-stage lower disc 29 at positions close to one side of the upper Petri dishes 6 held on the second holding units 33. The rotary cylinder 14 is moved up to thereby move the lower-stage upper disc 19 and the upper-stage upper disc 30 upward and the center shaft 15 is rotated to thereby rotationally displace the lower-stage lower disc 18 and the upper-stage lower disc 29 respectively relative to the lower-stage upper disc 19 and the upper-stage upper disc 30 by a predetermined angle, so that the top lids 5 and the top lids 7 are respectively shifted from the Petri dishes 4 and the upper Petri dishes 6. In such a state, the insertion holes 37 of the upper-stage upper disc 30, the through holes 39 of the upper-stage lower disc 29, and the insertion holes 24 of the lower-stage upper disc 19 vertically communicate with each other so that the suction tube 26 and the ejection tube 27 can be inserted thereinto.

Further, it is also possible that the size of the Petri dishes 4 on the lower stage and size of the upper Petri dishes 6 on the upper stage be equal to each other. Even when the top lids 5, 7 are opened, the positional relationship between the Petri dishes 4 on the lower stage and the Petri dishes 6 on the upper stage remains the same. Therefore, by previously shifting the positions of the Petri dishes 4 on the lower stage and the positions of the Petri dishes 6 on the upper stage from each other in the rotation direction, the Petri dishes 4 on the lower stage are also partially exposed. Thus, it is possible to replace the culture medium using the culture medium replacement means 13.

In the present embodiment, there has been described the structure having two upper and lower stages in which six Petri dishes can be set in each of the stages. However, the stages can be increased up to approximately four upper and lower stages in the same structure. Further, by limiting the number of Petri dishes that can be held in each stage, the number of stages can be further increased. On the other hand, when the number of stages is approximately two, the number of Petri dishes that can be held in each stage can be increased to, for example, eight. Also when the number of stages is increased, the lower-stage lower disc 18 which holds Petri dishes and odd-numbered discs from the bottom are connected to each other through the connection rods 31. Further, the escape holes 32 which allow the displacement of the connection rods 31 are formed on even-numbered discs from the bottom excepting the top disc, the even numbered discs holding the top lids. Further, holes having a function similar to the function of the insertion holes 24, 37 and the through holes 39 are formed on each of the discs excepting the bottom disc so that all Petri dishes located therebelow are partially exposed with the top lids laterally shifted and open. The number of Petri dishes in each stage and the number of stages are optimally set depending on the size of the Petri dishes and for efficiently using a space of the incubator chamber 1.

The culture medium replacement means 13 will be more specifically described with reference to FIGS. 1 and 2. A through hole 3A for introducing the suction tube 26 and the ejection tube 27 into the incubator chamber 1 is formed on the partition wall 3. A support rod 40 which is driven to move up and down by the linear actuator 28 provided in the drive chamber 2 is vertically arranged so as to pass through the through hole 3A. Further, a flange plate 41 is fixed to the lower end of the support rod 40 and located inside the incubator chamber 1, and the suction tube 26 and the ejection tube 27 are allowed to penetrate the flange plate 41 so as to be fixed thereto. When the support rod 40 is moved up, the through hole 3A can be closed in an air-tight state by the flange plate 41. Further, by moving the support rod 40 downward, the tips of the suction tube 26 and the ejection tube 27 can be introduced into the Petri dish 4 or the upper Petri dish 6. Specifically, an O-ring is fitted into an O-ring groove around the through hole 3A on the lower face of the partition wall 3 and the upper face of the flange plate 41 is pressed against the O-ring, thereby making it possible to air-tightly close the through hole 3A. A suction pump 42 is connected to the suction tube 26 inside the drive chamber 2, and an old culture medium is discharged to an external waste liquid tank. On the other hand, an ejection pump 43 is connected to the ejection tube 27 inside the drive chamber 2, and a new culture medium is supplied from a culture medium tank which is housed in an external cool box.

Figure 11:
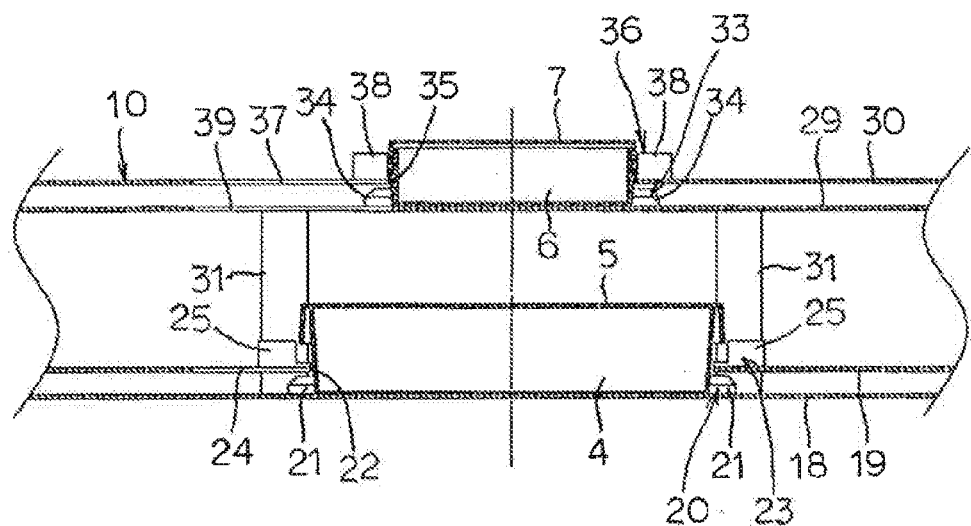
FIG. 11 is a partial cross-sectional view of a main part in a state in which the Petri dishes held on the holder are covered with the top lids.
Figure 12:
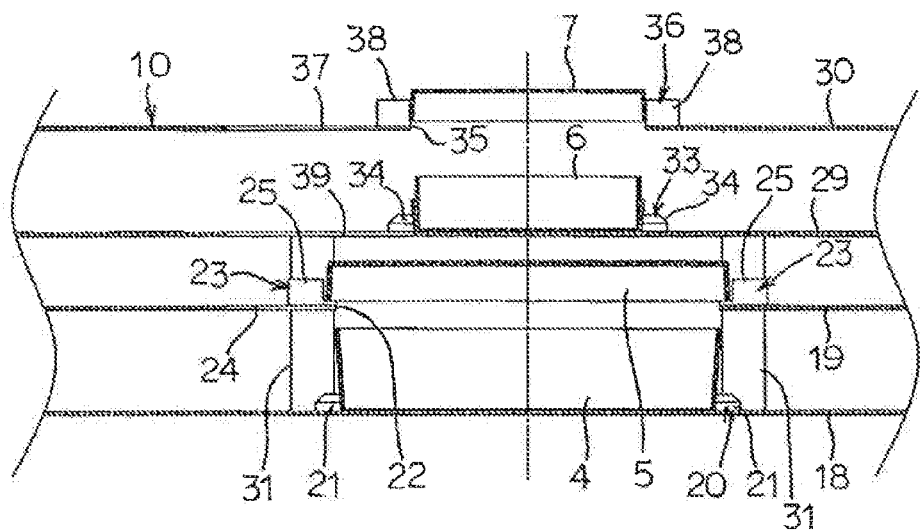
FIG. 12 is a partial cross-sectional view of a main part in a state in which the Petri dishes held on the holder and the top lids are vertically shifted from each other.
Figure 19:
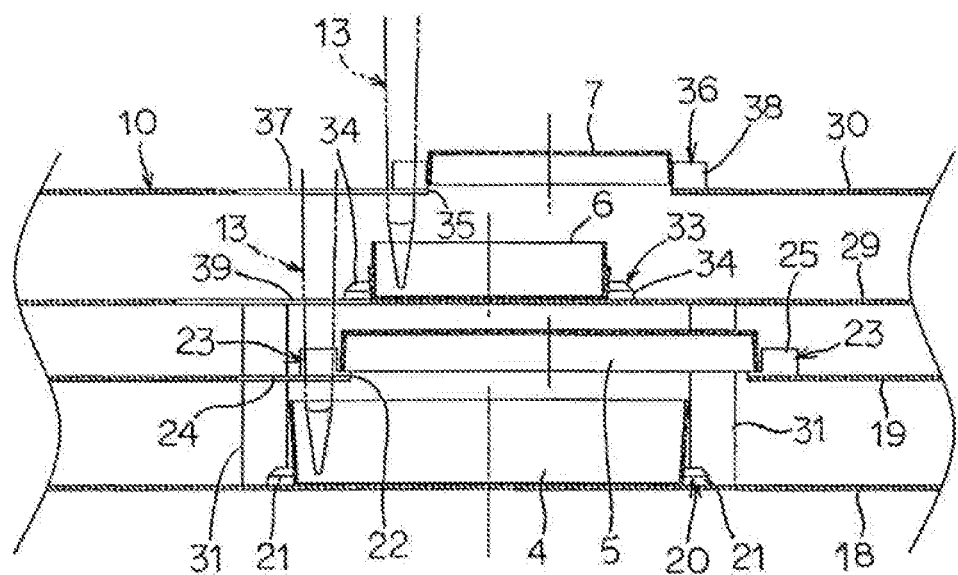
FIG. 19 is a perspective view illustrating a holder separated at a connection unit of a rotary shaft body.
Figure 14:
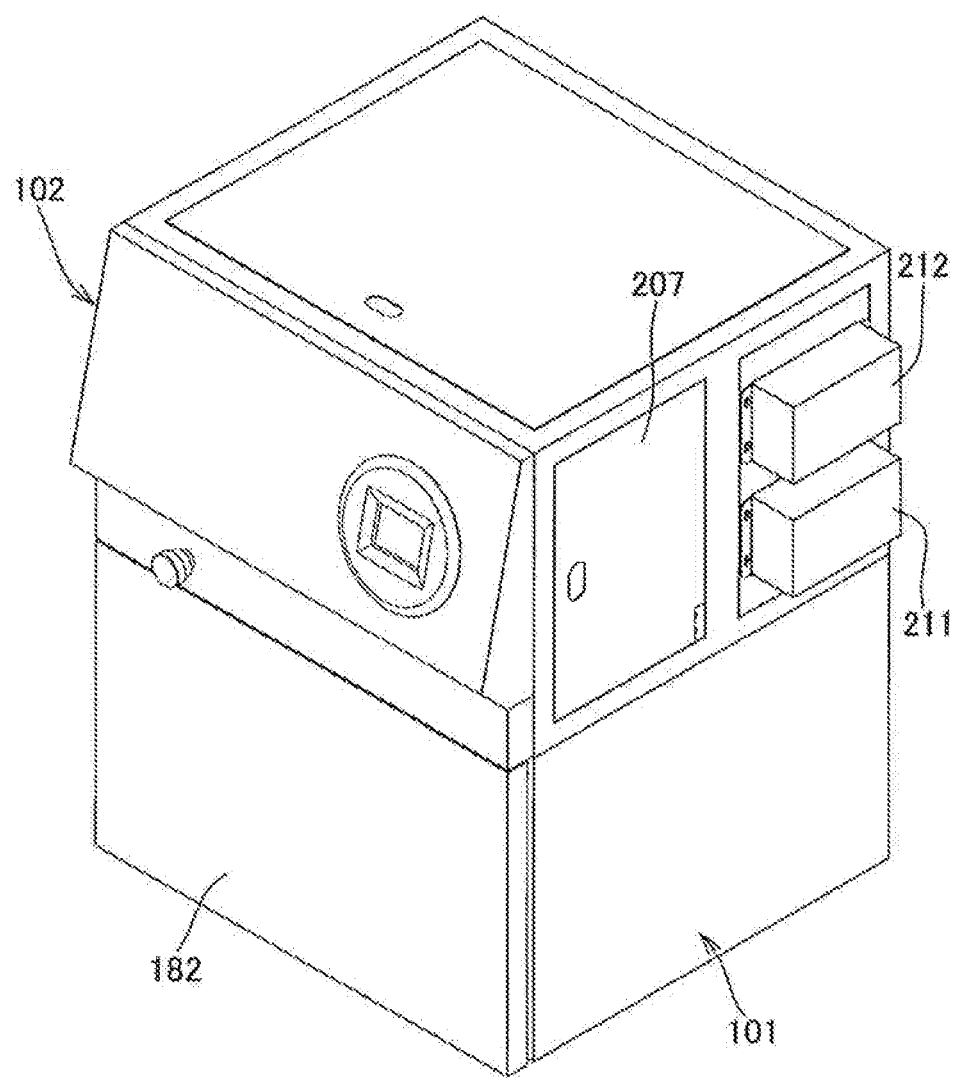
FIG. 14 is a perspective view illustrating a cell culture apparatus having a culture medium replacement function according to a second embodiment of the present invention.

Further, as illustrated in FIGS. 1 and 2, an L-shaped guide groove 44 which has a vertical portion 44A and a horizontal portion 44B is formed on the rotary cylinder 14, and a pin 45 which is provided in a projecting manner in the center shaft 15 is engaged with the guide groove 44, so that the rotary cylinder 14 and the center shaft 15 can be integrally rotated (synchronous rotation means), and the center shaft 15 can be rotationally displaced by a predetermined rotation angle relative to the rotary cylinder 14. More specifically, when the pin 45 is located on the upper part of the vertical portion 44A of the guide groove 44, the upper discs 19, 30 are located on their lowest positions and the Petri dishes 4 and the upper Petri dishes 6 are respectively covered with the top lids 5 and the top lids 7. Further, when the center shaft 15 is driven to rotate, the rotary cylinder 14 is integrally rotatable with the center shaft 15 (see FIG. 11). Then, when the linear actuator 12 is driven to move the rotary cylinder 14 upward, the pin 45 is located on the lower end of the vertical portion 44A of the guide groove 44, that is, one end of the horizontal portion 44B, and the top lids 5, 7 are thereby lifted up (see FIG. 12). When the center shaft 15 is driven to rotate in this state, it is possible to rotate only the center shaft 15 by a predetermined angle while maintaining the rotary cylinder 14 in a stationary state by the rotation restriction means until the pin 45 reaches the other end of the horizontal portion 44B of the guide groove 44, and thereby shift the top lids 5 and 7 respectively from the Petri dishes 4 and the upper Petri dishes 6 (see FIG. 13). Further, the bearing unit 9 may have a braking function and a clamp mechanism that restricts only the rotation of the rotary cylinder 14 may be provided at an appropriate position instead of using the guide groove 44 and the pin 45. Further, an interlocking mechanism that is engaged and disengaged between the rotary cylinder 14 and the center shaft 15 may be provided so that the rotary cylinder 14 and the center shaft 15 can integrally rotate with each other.

As illustrated in FIGS. 1 and 3 to 6, an opening/closing door 46 is provided on the front of the incubator chamber 1. Cutout portions 47 to 50 are formed so that, when the positions of the holding units 20, 33 of the lower discs 18, 29 and the top lid holding units 23, 36 of the upper discs 19, 30 are vertically aligned to each other, fingers can pass from the outer peripheral parts through the holding units 20, 33 and the top lid holding units 23, 36. The cutout portions 48 of the upper disc 19 and the cutout portions 50 of the upper disc 30 respectively communicate with the openings 22 and the openings 35. Accordingly, when cells and a culture medium are first put in the Petri dish 4 and the Petri dish 4 is covered with the top lid 5, the opening/closing door 46 is opened, and the Petri dish 4 and the top lid 5 are pinched with fingers and set in the holder 10, the fingers can be allowed to advance toward the centers of the discs by virtue of the cutout portions 47, 48 of the lower disc 18 and the upper disc 19. Then, by dropping the Petri dish 4 through the opening 22 of the upper disc 19, the Petri dish 4 is held by the holding unit 20 of the lower disc 18, and the top lid 5 is held by the top lid holding unit 23 of the upper disc 19. Therefore, an operation for setting the Petri dish 4 can be made extremely easy. An operation for setting the upper Petri dish 6 and the top lid 7 on the holder 10 on the upper stage can be performed in the same manner.

Figure 7:
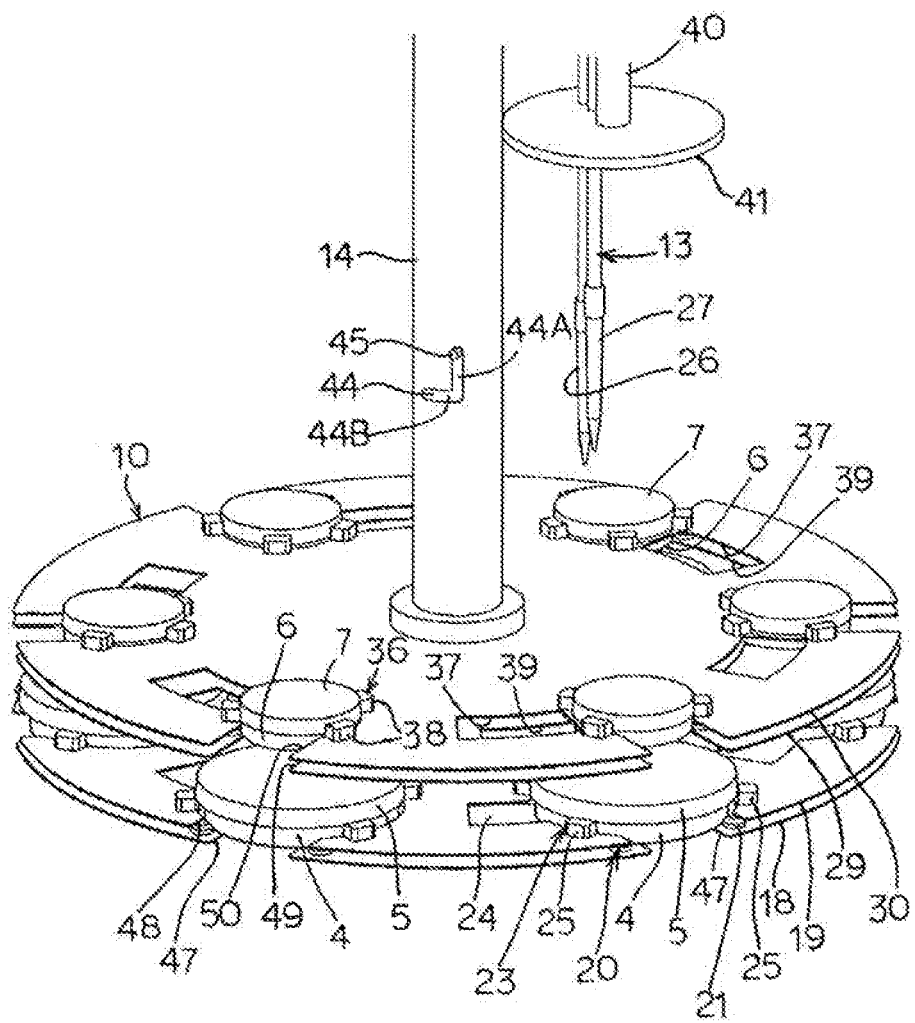
FIG. 7 is a partial perspective view illustrating a state in which culture is performed with the Petri dishes set on a holder in an incubator chamber.
Figure 8:
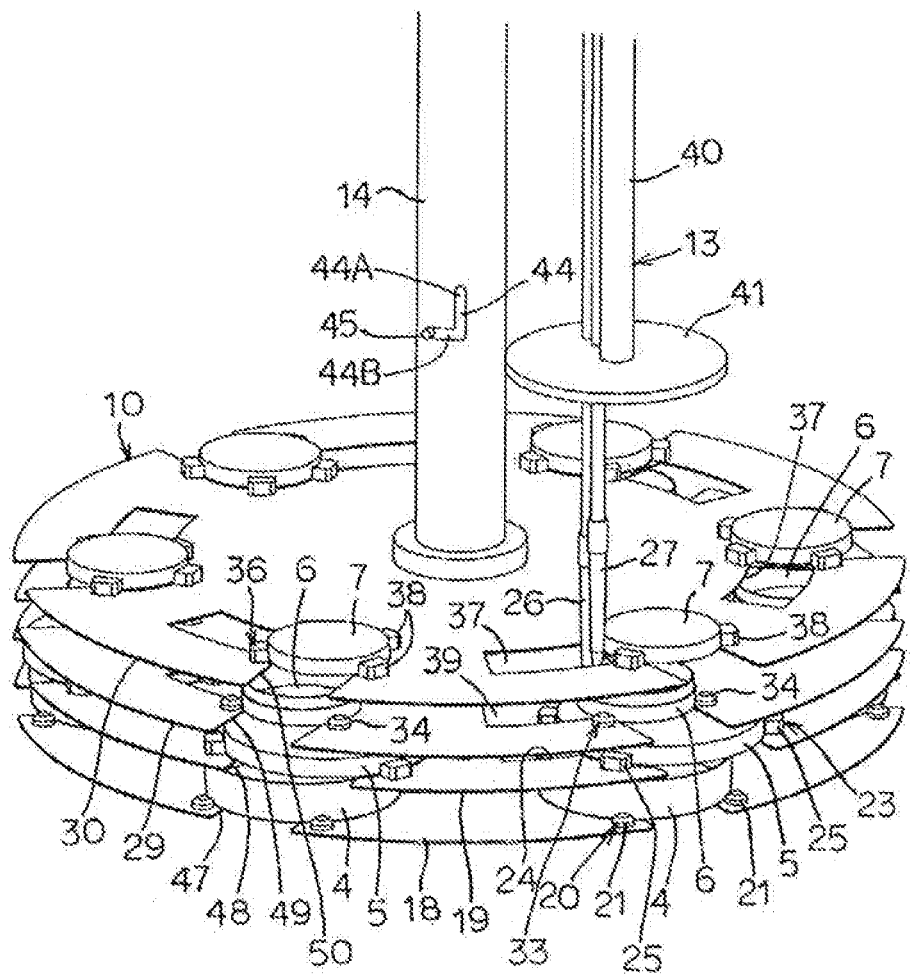
FIG. 8 is a partial perspective view illustrating a state in which the top lids are shifted from the Petri dishes and a culture medium in a Petri dish on the lower stage is being replaced.
Figure 9:
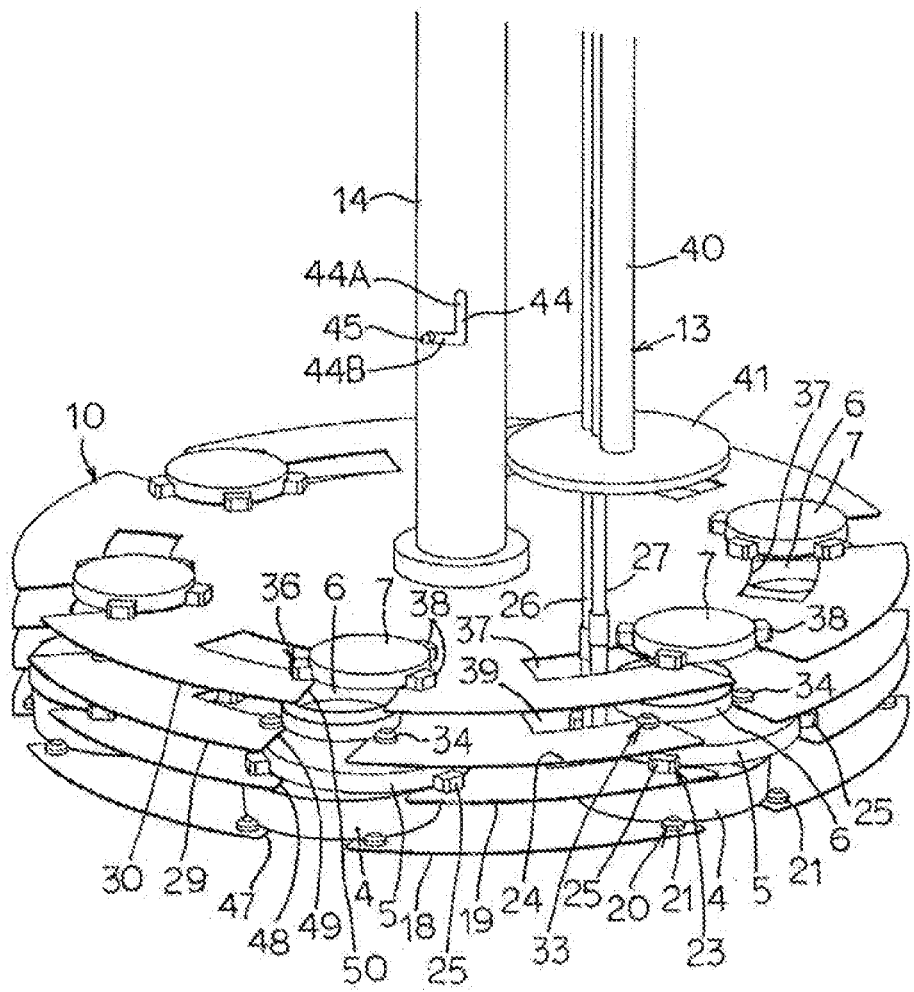
FIG. 9 is a partial perspective view illustrating a state in which the top lids are shifted from the upper Petri dishes and a culture medium in an upper Petri dish on the upper stage is being replaced.
Figure 10:
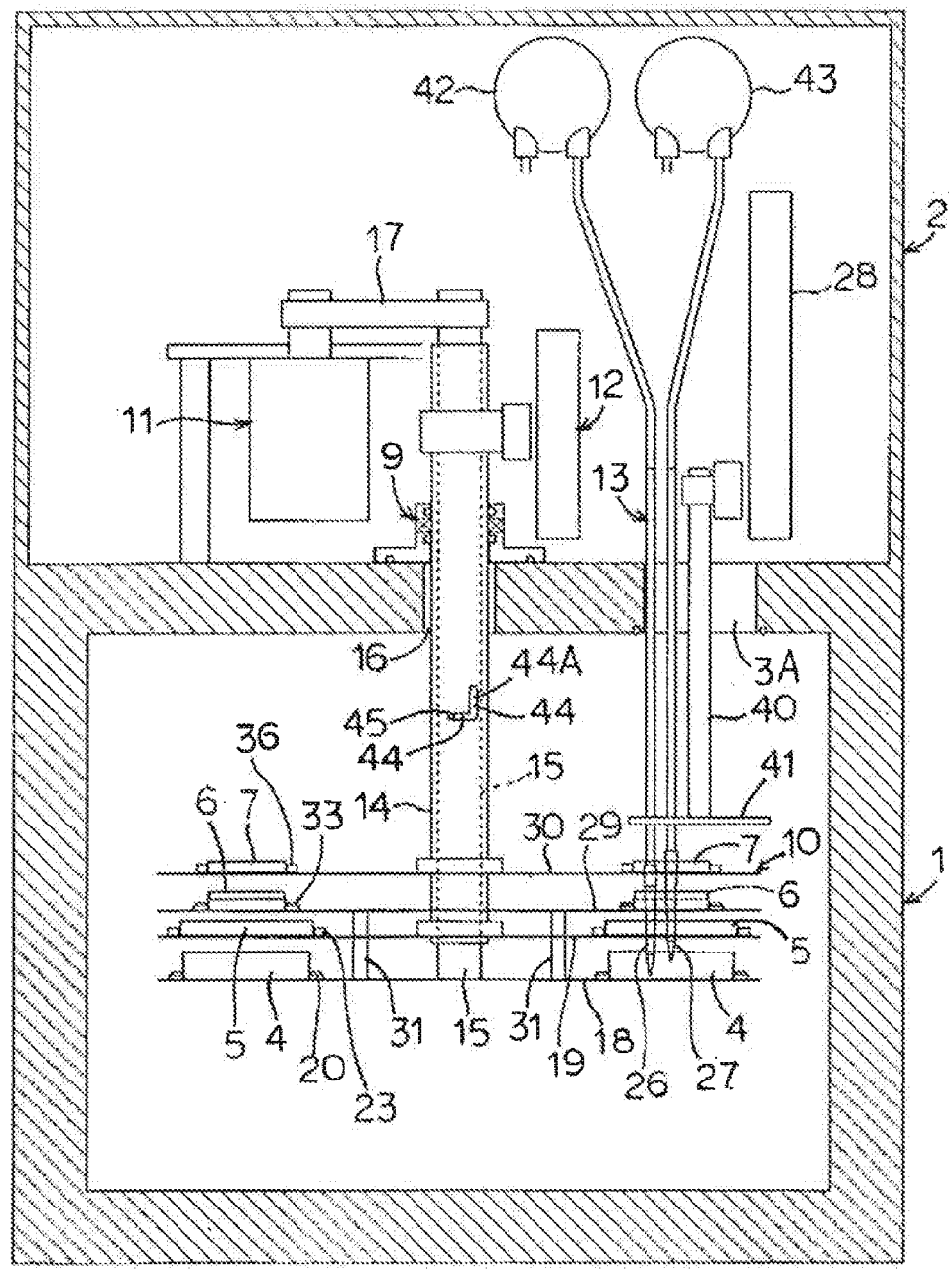
FIG. 10 is an entire simplified cross-sectional view of the state of FIG. 8.

FIG. 7 illustrates a state in which the Petri dishes 4 are covered with the top lids 5 and the upper Petri dishes 6 are covered with the top lids 7. In this state, the suction tube 26 and the ejection tube 27 of the culture medium replacement means 13 are moved up, and the through hole 3A is closed in an air-tight state by the flange plate 41. Therefore, cells can be cultured with the inside of the incubator chamber 1 filled with a desired gas at an appropriate temperature and an appropriate humidity. FIGS. 8 and 9 illustrate a state in which an operation for replacing the culture medium is being performed with the top lids 5 laterally shifted from the Petri dishes 4 and, at the same time, the top lids 7 laterally shifted from the upper Petri dishes 6. Further, the insertion holes 37 of the upper-stage upper disc 30, the through holes 39 of the upper-stage lower disc 29, and the insertion holes 24 of the lower-stage upper disc 19 vertically communicate with each other, and the Petri dishes 4 and the Petri dishes 6 are partially exposed. FIGS. 8 and 10 illustrate a state in which the tips of the suction tube 26 and the ejection tube 27 are located inside a Petri dish 4 on the lower stage through an insertion hole 37, a through hole 39, and an insertion hole 24, and the replacement of the culture medium is being performed. FIG. 9 illustrates a state in which the tips of the suction tube 26 and the ejection tube 27 are located inside an upper Petri dish 6 through an insertion hole 37, and the replacement of the culture medium is being performed.

In order to replace the culture medium in a Petri dish 4 or an upper Petri dish 6 located at another position, the center shaft 15 is rotated by a predetermined angle by the drive motor 11 with the Petri dishes 4 covered with the top lids 5 and the upper Petri dishes 6 covered with the top lids 7 to thereby align the position of the target Petri dish 4 or the target Petri dish 6 with the positions of the suction tube 26 and the ejection tube 27. Thereafter, as described above, the rotary cylinder 14 is moved upward, and the center shaft 15 is then rotated by a predetermined angle to thereby laterally shift the top lids 5, 7 so that the Petri dishes 4 and the upper Petri dishes 6 are partially exposed. Further, in order to accurately control the holder 10 to rotate, it is also preferred to apply a marker onto an appropriate position and the marker is read by a sensor to thereby perform feedback control.

Next, a cell culture apparatus having a culture medium replacement function according to a second embodiment of the present invention will be described with reference to FIGS. 14 to 28. In the drawings, reference numeral 101 denotes an incubator chamber, 102 denotes a drive chamber, 103 denotes a partition wall, 104 denotes a Petri dish, 105 denotes a top lid, 106 denotes a lower disc, 107 denotes an upper disc, 108 denotes a rotary shaft body, 109 denotes a bearing unit, 110 denotes a holder, 111 denotes a drive motor, 112 denotes a linear actuator, and 113 denotes culture medium replacement means.

Also in the present embodiment, a basic operation is the same as the operation in the first embodiment. Specifically, the cell culture apparatus of the present embodiment has the following configuration. At least a set of an upper disc 107 and a lower disc 106 each fixed to a rotatable shaft is horizontally arranged inside the incubator chamber 101. The Petri dishes 4 in each of which cells and a culture medium are put are held on the lower disc 106, and the top lids 105 are held on the upper disc 107. The lower side of each of the top lids 105 is open. It is possible to achieve a state in which the lower disc 106 and the upper disc 107 are brought vertically close to each other to thereby cover the Petri dishes 104 with the top lids 105 and a state in which the lower disc 106 and the upper disc 107 are vertically separated from each other and one of them is rotated by a predetermined angle to thereby laterally shift the top lids 105 from the Petri dishes 104 so that the Petri dishes 104 are partially exposed. At this point, the culture medium replacement means 113 is inserted through an insertion hole 124 formed on the upper disc 107 from the upper side into the exposed portion of a Petri dish 104. After replacing the culture medium, the culture medium replacement means 113 is retracted. Then, the lower disc 106 and the upper disc 107 are rotated and vertically moved to cover the Petri dishes 104 with the top lids 105, thereby continuing the cell culture. In the present embodiment, the lower disc 106 which holds the Petri dishes 104 and the upper disc 107 which holds the top lids 105 of the Petri dishes 104 are defined as one set, and four sets are used and vertically arranged in four stages. The same lower disc 106 and the same upper disc 107 are used in each of the four stages. Therefore, in the present embodiment, all of the Petri dishes 104 have the same size.

Specifically, the cell culture apparatus of the present embodiment has the following configuration. The incubator chamber 101 and the drive chamber 102 located above the incubator chamber 101 are arranged with the partition wall 103 interposed therebetween. The rotary shaft body 108 includes a first shaft body 114 and a second shaft body 115 which both have the same rotation center and are concentrically arranged. The first shaft body 114 is slidable in the axial direction relative to the second shaft body 115, and the first shaft body 114 and the second shaft body 115 are relatively rotatable to each other by a predetermined angle. The rotary shaft body 108 is allowed to vertically pass through a shaft hole 116 which is formed on the partition wall 103 and supported by the bearing unit 109. The second shaft body 115 of the rotary shaft body 108 is supported so as to be rotatable at a fixed position and driven to rotate by the drive motor 111 which is arranged inside the drive chamber 102. The first shaft body 114 of the rotary shaft body 108 is driven to move up and down in the vertical direction by the linear actuator 112 which is arranged inside the drive chamber 102. Inside the incubator chamber 101, the lower disc 106 which holds the Petri dishes 104 is directly or indirectly concentrically fixed to the lower part of the second shaft body 115 and the upper disc 107 which holds the top lids 105 of the Petri dishes 104 is directly or indirectly concentrically fixed to the lower part of the first shaft 114. In the lower disc 106, a plurality of holding units 120 which mount thereon and hold the Petri dishes 4 are provided on the same circumference at every constant rotation angle. Openings 122 which receive the Petri dishes 104 are formed on the upper disc 107 so that the center of each of the openings 122 is located at same position as the center of the corresponding holding unit 120. Top lid holding units 123 which hold the outer peripheral parts of the top lids 105 of the Petri dishes 104 are provided on the peripheral edges of the respective openings 122. Further, insertion holes 124 are formed to penetrate the upper disc 107 at positions close to one side of the top lids 105 held by the top lid holding units 123. A suction tube 126 and an ejection tube 127 which constitute the culture medium replacement means 113 are allowed to penetrate the partition wall 103 so as to hang down to the incubator chamber 101, and driven to move up and down by a linear actuator 128 which is provided inside the drive chamber 102. Cells are cultured in a state in which the upper disc 107 is moved down with the relative rotation angle between the upper disc 107 and the lower disc 106 maintained zero to thereby cover the Petri dishes 104 with the top lids 105. Thereafter, the upper disc 107 is moved up, and the lower disc 106 is rotationally displaced by a predetermined angle relative to the upper disc 107 to thereby shift the top lids 105 from the Petri dishes 104. In this state, the suction tube 126 and the ejection tube 127 are moved down so that the tips thereof are located inside the Petri dish 4 through the insertion hole 124 of the upper disc 107. An old culture medium is discharged using the suction tube 126, and a new culture medium is then injected from the ejection tube 127 to thereby automatically replace the culture medium.

More specifically, as illustrated in FIGS. 15 to 18, the rotary shaft body 108 has a structure in which the first shaft body 114 passes through the inside of the cylindrical second shaft body 115 so as to be vertically slidable and freely rotatable by slidable bushes 118, 118 above a part held by the bearing unit 109 having a sleeve-like shape. The second shaft body 115 is supported by the bearing unit 109 so as to be rotatable at a fixed position using bearings 119, 119. A timing belt 117 is wound around a pulley 129 which is fixed to the upper end part of the second shaft body 115, the upper end part projecting upward from the bearing unit 109, and a pulley 130 which is fixed to a drive shaft of the drive motor 111 to drive the pulleys 129, 130 to rotate. Gas seals are provided between the bearing unit 109 and the second shaft body 115 and between the second shaft body 115 and the first shaft body 114 so that the incubator chamber 101 has air-tightness. A stepping motor which can control the rotation angle with high accuracy is used as the drive motor 111 in order to open/close the top lids 105 and stop the Petri dishes 104 at accurate rotation positions with respect to the suction tube 126 and the ejection tube 127 of the culture medium replacement means 113. Further, the upper end part of the first shaft body 114, the upper end part projecting above the second shaft body 115, is connected to a drive unit 132 of the linear actuator 112 through a rotary joint 131.

The rotary shaft body 108 which is located inside the incubator chamber 101 is provided with a connection unit 133 which is located above the upper disc 107 on the highest stage and capable of vertically separating and connecting the first shaft body 114 and the second shaft body 115. The first shaft body 114 of the rotary shaft body 108 is formed into a cylindrical shape from the connection unit 133, and the second shaft body 115 is located inside the first shaft body 114. That is, as illustrated in FIGS. 16 and 18 to 25, in the lower part of the rotary shaft body 108 located inside the incubator chamber 101, the first shaft body 114 constitutes a cylindrical outer shaft portion 134 and the second shaft body 115 constitutes an inner shaft portion 135 located inside the outer shaft portion 134. Further, the upper disc 107 is fixed to a plurality of fixation pieces 136 which are provided in a projecting manner on the outer periphery of the outer shaft portion 134. The lower disc 106 is fixed to a plurality of fixation pieces 138 which are provided in a projecting manner on the outer periphery of the inner shaft portion 135 and project outward in the radial direction through a plurality of opening portions 137 formed on the outer shaft portion 134. The opening portions 137 have a size that allows the fixation pieces 138 of the inner shaft portion 135 to relatively move upward and displace by a predetermined rotation angle inside thereof at the time of an operation for opening the top lids 105. The inner-outer relationship between the first shaft body 114 and the second shaft body 115 may be an inverse relationship thereof. Further, the lower disc 106 on the lowest stage is mounted on and fixed to a fixation disc 139 which is fixed to the lower end part of the inner shaft portion 135.

The structure of the connection unit 133 of the rotary shaft body 108 will be described with reference to FIGS. 16 and 19 to 21. The holder 110 which holds the Petri dishes 104 and the top lids 105 is provided below the connection unit 133. The first shaft body 114 includes a center shaft 140 which is located above the connection unit 133 and the outer shaft portion 134 which is located below the connection unit 133. The second shaft body 115 includes a cylindrical drive shaft 141 which is located above the connection unit 133 and the inner shaft portion 135 which is located below the connection unit 133. The end face of a cylindrical outer-inner conversion member 142, the end face facing the radial direction, is fixed to the lower end of the drive shaft 141. A circular hole 143 is formed on the central part of the end face, and the lower end part of the center shaft 140 is inserted through the circular hole 143 with some clearance existing therebetween. The lower end of the outer-inner conversion member 142 is open, and openings 145 are formed on a cylindrical portion 144 at 120° intervals. The central part of an inner-outer conversion member 146 is fixed to the lower end of the center shaft 140, and three connection pieces 147 which radially extend from the central part of the inner-outer conversion member 146 are allowed to project outward through the openings 145 of the outer-inner conversion member 142. The connection unit 133 is further provided with a columnar inner connection member 148 and a cylindrical outer connection member 149 inside which the inner connection member 148 is located. The inner connection member 148 and the outer connection member 149 are each divided into two parts each including a semicircular portion in the radial direction and a vertical portion in the axial direction and having substantially the same shape, and the two parts can be laterally joined to each other. An upper portion 148A of the inner connection member 148 is fixed to the lower end of the cylindrical portion 144 of the outer-inner conversion member 142. An upper portion 149A of the outer connection member 149 is fixed to the connection pieces 147 of the inner-outer conversion member 146. The outer diameter of the outer-inner conversion member 142 is substantially equal to the outer diameter of the inner connection member 148. A lower portion 148B of the inner connection member 148 constitutes a part of the inner shaft portion 135. On the other hand, a lower portion 149B of the outer connection member 149 constitutes a part of the outer shaft portion 134. The upper portion 148A and the lower portion 148B of the inner connection member 148 are detachably connected to each other with a single connection screw 150 which is inserted from the lateral side of the lower portion 148B into the central part thereof. The upper portion 149A and the lower portion 149B of the outer connection member 149 are detachably connected to each other with two connection screws 151, 151 which are inserted from the lateral side of the lower portion 149B into both sides thereof. Further, a cutout 152 is formed on the cylindrical portion of the lower portion 149B of the outer connection member 149 so as to prevent the interference to the connection screw 150 when moving the first shaft body 114 upward.

Next, the outer shaft portion 134 and the inner shaft portion 135 will be described with reference to FIGS. 16 and 20 to 23. In the outer shaft portion 134, a spacer cylinder 153 having a cylindrical shape and an upper fixation member 154 which has the fixation pieces 136 projecting in four directions are used depending on the number of stages. Specifically, the number of upper fixation members 154 is equal to the number of stages, and the number of spacer cylinders 153 is smaller than the number of stages by one. The spacer cylinder 153 has the four opening portions 137 which are formed on the cylindrical portion at 90° intervals and open downward. Further, an engagement step portion 156 is formed on the upper end face of the spacer cylinder 153 and a ring portion 155 of the upper fixation member 154 is engaged with the engagement step portion 156. An engagement step portion similar to the engagement step portion 156 is formed also on the lower end of the cylindrical portion of the spacer cylinder 153. The upper fixation member 154 has a structure in which the fixation pieces 136 are provided in a projecting manner on the outer periphery of the ring portion 155 on the central part thereof. The upper fixation member 154 located on the lowest stage (the lowest upper fixation member 154) is manufactured to be thicker than the other upper fixation members 154. The cylindrical portion of the spacer cylinder 153 is mounted on the upper face of the ring portion 155 of the lowest upper fixation member 154, and fixation screws 157 which penetrate the cylindrical portion from the upper side are screwed with the ring portion 155 to thereby connect the lowest upper fixation member 154 and the spacer cylinder 153 to each other. Then, the ring portion 155 of the upper fixation member 154 located on the second stage from the bottom (the second-lowest upper fixation member 154) is engaged with the engagement step portion 156 of the above spacer 153, and the cylindrical portion of another spacer cylinder 153 is mounted thereon. Further, the fixation screws 157 which penetrate the cylindrical portion from the upper side are screwed with the cylindrical portion of the lower spacer cylinder 153 to thereby sandwich the ring portion 155 of the upper fixation member 154 between the upper and lower spacer cylinders 153, 153 so as to be fixed. Such an operation is repeatedly performed toward the upper stages to perform the connection, thereby assembling the outer shaft portion 134. Further, the spacer cylinder 153 and the upper fixation member 154 are accurately fixed at a position displaced in one rotation direction by a certain angle in each stage.

In the inner shaft portion 135, a single connection shaft 158, and a spacer shaft 159 and a lower fixation member 160 having the fixation pieces 138 projecting in four directions which are both externally fitted onto and fixed to the connection shaft 158 are used depending on the number of stages. However, the fixation disc 139 is used instead of the lower fixation member 160 located on the lowest stage. Therefore, the number of sets of the spacer shafts 159 and the lower fixation members 160 to be used is smaller than the number of stages by one. The spacer shaft 159 is a columnar shaft in which an insertion hole 161 into which the connection shaft 158 is fitted is formed on the center thereof. The spacer shaft 159 is fixed to the connection shaft 158 by inserting the connection shaft 158 through the insertion hole 161 and engaging the tip of a fixation screw 162 screwed from the outer peripheral face of the spacer shaft 159 with an engagement hole 163 of the connection shaft 158. Then, the lower end part of the connection shaft 158 is allowed to pass through a center hole 164 of the fixation disc 139 so that the fixation disc 139 is joined to the lower face of the spacer shaft 159, and the fixation disc 139 and the spacer shaft 159 are fixed to each other with a screw from the lower side. The lower fixation member 160 has a structure in which the fixation pieces 138 are formed in a projecting manner on the outer periphery of a center disc 165 which has an outer diameter substantially equal to the outer diameter of the space shaft 159, and a center hole 166 is formed on the center disc 165. Then, the lower fixation member 160 is placed from the upper side of the connection shaft 158 so as to allow the connection shaft 158 to pass through the center hole 166 of the lower fixation member 160 to thereby join the center disc 165 to the upper face of the spacer shaft 159. Then, the center disc 165 is fixed to the spacer shaft 159 with fixation screws 167, 167 which penetrate the center disc 165. Such an operation is repeatedly performed to the upper stages to perform the connection, thereby assembling the inner shaft portion 135. In practice, the inner shaft portion 135 is assembled so that the fixation pieces 138 of the lower fixation member 160 project outward through the opening portions 137 of the spacer cylinder 153 of the outer shaft portion 134. Therefore, the spacer cylinder 153 and the upper fixation member 154 are assembled to each other immediately after the spacer shaft 159 and the lower fixation member 160 are assembled to each other, and these assembling operations are alternatively performed. Although the fixation disc 139, and the upper fixation member 154 and the spacer shaft 159 on the lowest stage have a special shape, the other members may be added depending on the number of stages.

Further, the lower portion 149B of the outer connection member 149 of the connection unit 133 is fixed to the upper end face of the spacer cylinder 153 on the highest stage with a screw from the upper side. In addition, the lower portion 148B of the inner connection member 148 is fixed to the upper end face of the connection shaft 158 with a screw. In order to accurately assemble the members which constitute the rotary shaft body 108, there is employed a structure in which, in two members to be joined to each other, a pin provided in a projecting manner on a joint surface of one of the members is fitted with a hole formed on a joint surface of the other member.

Further, as illustrated in FIGS. 15 to 25, the central part of the lower disc 106 is mounted on and attached to the fixation disc 139 and the fixation pieces 138 of the lower fixation member 160 of the inner shaft portion 135. Further, the central part of the upper disc 107 is mounted on and attached to the fixation pieces 136 of the upper fixation member 154 of the outer shaft portion 134.

Figure 25:
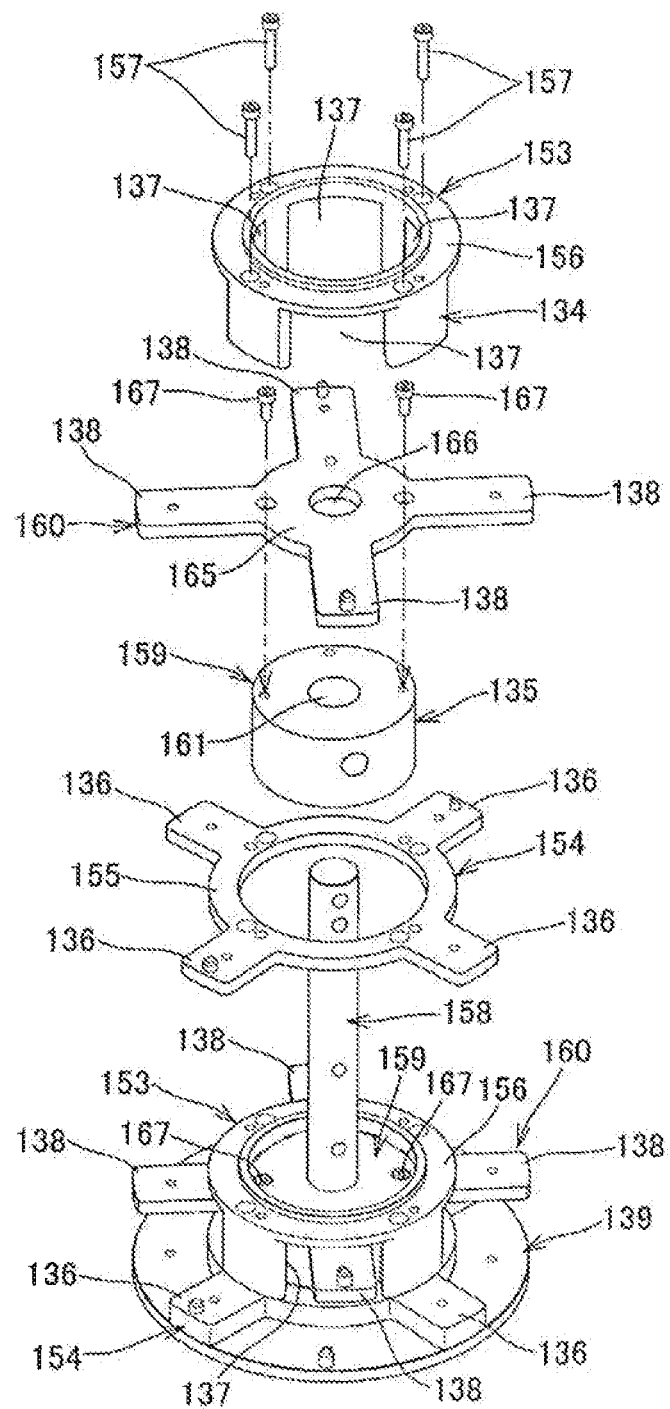
FIG. 25 is an exploded perspective view illustrating the set of the lower disc and the upper disc on the lowest stage.
Figure 24:
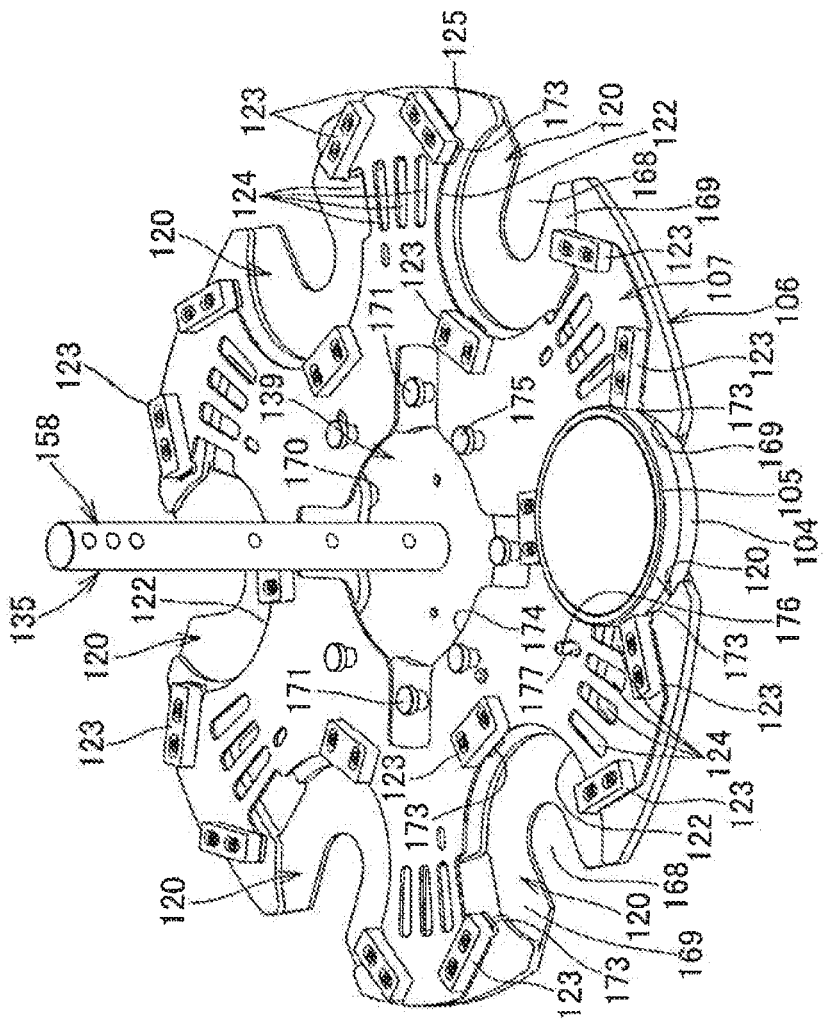
FIG. 24 is a partial perspective view illustrating one set of a lower disc and an upper disc on the lowest stage.
Figure 25:
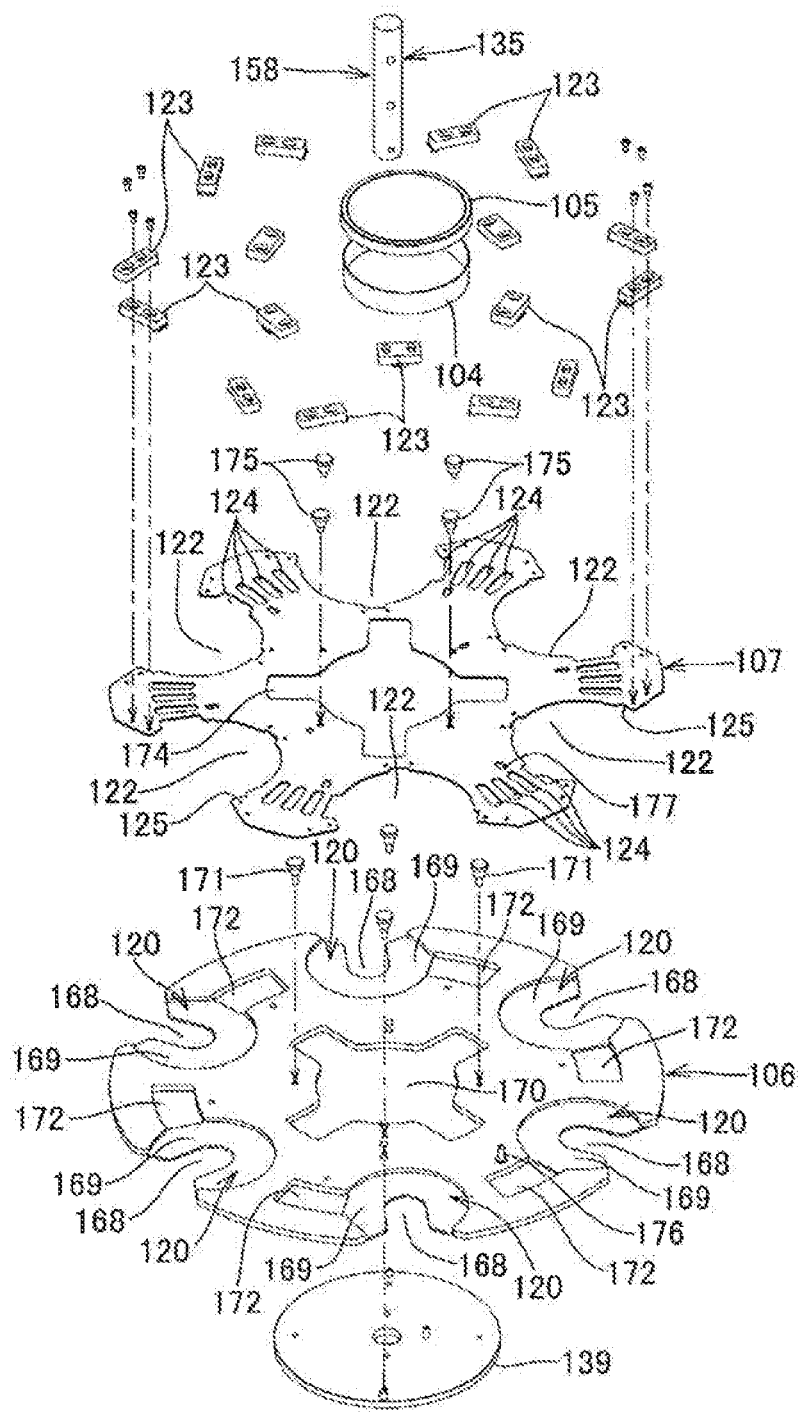
Figure 26:
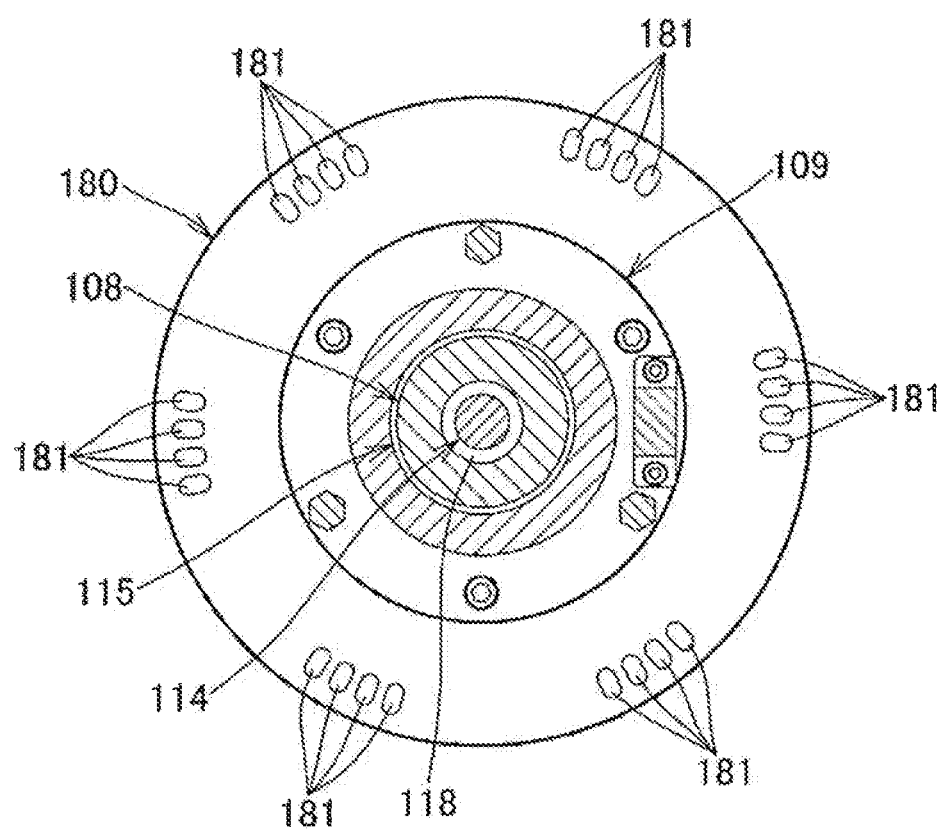
FIG. 26 is a transverse sectional view of the rotary shaft body illustrating the structure of a control plate of rotation restriction means.

Next, the lower disc 106 and the upper disc 107 will be described in detail with reference to FIGS. 24 and 25. In the lower disc 106, the six holding units 120 which mount thereon and hold the Petri dishes 104 are provided on the same circumference at every constant rotation angle, and cutout portions 168 which have a U-shape in plan view and allow fingers to pass through are formed from the outer peripheral part to the respective holding units 120. In the present embodiment, each of the holding units 120 of the lower disc 106 is a recessed step portion 169 which is formed on the upper face of the surrounding area of the cutout portion 168 and receives the bottom part of the Petri dish 104. Further, the recessed step portion 169 has a circular shape having a center angle larger than 180° for receiving the bottom part of the Petri dish 104 without position shift. An attachment opening 170 having a generally X-shape is formed on the central part of the lower disc 106, and the upper fixation member 154 of the outer shaft portion 134 can be inserted through the attachment opening 170. Accordingly, even after the outer shaft portion 134 and the inner shaft portion 135 both located below the connection unit 133 are assembled, the attachment opening 170 of the lower disc 106 is allowed to externally pass through the outer shaft portion 134 from the upper side, and sequentially pass through the fixation pieces 136 and the fixation pieces 138 so that a part other than the attachment opening 170 is mounted on the fixation disc 139 on the lowest stage or the fixation pieces 138 of another lower fixation member 160, and attached thereto with fastening screws 171. Further, a through hole 172 which extends in the circumferential direction and has a generally quadrangular shape is formed on one side of each of the holding units 120 of the lower disc 106, and the suction tube 126 and the ejection tube 127 for sucking and ejecting the culture medium which constitute the culture medium replacement means 113 can be inserted through the through hole 172. In order to accurately assemble the lower disc 106 to the fixation disc 139 on the lowest stage and the fixation pieces 138 of another lower fixation member 160, there is employed a structure in which pins which are provided in a projecting manner in the fixation disc 139 and the fixation pieces 138 are fitted with holes which are formed by piercing on the lower disc 106.

The openings 122 which receive the Petri dishes 104 are formed on the upper disc 107 so that the center of each of the openings 122 is located at same position as the center of the corresponding holding unit 120. In addition, the top lid holding units 123 which hold the outer peripheral parts of the top lids 105 of the Petri dishes 104 are provided on the peripheral edges of the respective openings 122. Further, the insertion holes 124 are formed to penetrate the upper disc 107 at positions close to one side of the top lids 105 held by the top lid holding units 123. Four insertion holes 124 are independently formed corresponding to Petri dishes 104 of the respective stages. The suction tube 126 and the ejection tube 127 for sucking and ejecting the culture medium which constitute the culture medium replacement means 113 are inserted through each of the insertion holes 124 so as to be able to access each of the Petri dishes 104. However, the insertion hole 124 that is located closest to the top lid 105 is formed continuous with the corresponding opening 122. A cutout portion 125 is formed on the outer periphery of each of the openings 122 to thereby allow the opening 122 to communicate with the outside so that, when the Petri dish 104 covered with the top lid 105 is pinched with fingers from the upper and lower sides, the fingers can pass through the cutout portion 168 and the cutout portion 125. Each of the top lid holding units 123 of the upper disc 107 is a machined component or molded component made of synthetic resin, and has a locking claw 173 on one end thereof. The locking claw 173 abuttingly locks the outer peripheral face of the top lid 105 of the Petri dish 104, and the lower edge of the top lid 105 is mounted on the locking claw 173 to support. Three top lid holding units 123 are arranged on the peripheral edge of each of the openings 122 so that the top lid 105 can be held without backlash. Further, an attachment opening 174 which has the same shape as the attachment opening 170 of the lower disc 106 is formed on the central part of the upper disc 107. As with the lower disc 106, also in the upper disc 107, the attachment opening 174 is allowed to externally pass through the outer shaft portion 134, and a part other than the attachment opening 174 is mounted on the fixation pieces 136 of the upper fixation member 154 and attached thereto with fastening screws 175.

In order to accurately assemble the upper disc 107 to the fixation pieces 136 of the upper fixation member 154, there is employed a structure in which pins which are provided in a projecting manner in the fixation pieces 136 are fitted with holes which are formed by piercing on the lower disc 106.

Further, in the present embodiment, there is provided synchronous rotation means which functions in a state in which the upper disc 107 is moved down with the relative rotation angle between the upper disc 107 and the lower disc 106 maintained zero to cover the Petri dishes 104 with the top lids 105 and integrates the upper disc 107 and the lower disc 106 with each other with respect to rotation. Specifically, as illustrated in FIGS. 24 and 25, the synchronous rotation means is configured in such a manner that, in one set of the upper disc 107 and the lower disc 106 on the lowest stage, a pin 176 is provided on the upper face of the lower disc 106 so as to project upward, and, on the other hand, an engagement hole 177 with which the pin 176 is engaged is formed on the upper disc 107. When the top lids 105 are put on the Petri dishes 104, the pin 176 is engaged with the engagement hole 177 in an operation of moving the upper disc 107 downward. Thereafter, by driving the second shaft body 115, that is, the inner shaft portion 135 to rotate to thereby rotate the lower disc 106, the upper disc 107 also rotates integrally therewith.

Further, in the present embodiment, there is provided rotation restriction means which functions in a state in which the upper disc 107 is moved upward to thereby remove the top lids 105 from the Petri dishes 104, and prevents the rotation of the upper disc 107. Specifically, as illustrated in FIGS. 16, 18, 19, and 26, the rotation restriction means is configured in such a manner that one of the connection pieces 147 of the inner-outer conversion member 146 of the first shaft body 114 is extended outward to form an extended portion 178, a pin 179 is provided on the upper face of the tip of the extended portion 178 so as to project upward, and engagement holes 181 with which the pin 179 is engaged are formed at six positions in the circumferential direction of a circular control plate 180 which is fixed to the lower end of the bearing unit 109. In the control plate 180, four of the engagement holes 181 are formed at each of the six positions at regular intervals in the circumferential direction, and the four engagement holes 181 correspond to stopping positions of Petri dishes 104 on the respective stages when replacing the culture medium.

Figure 27:
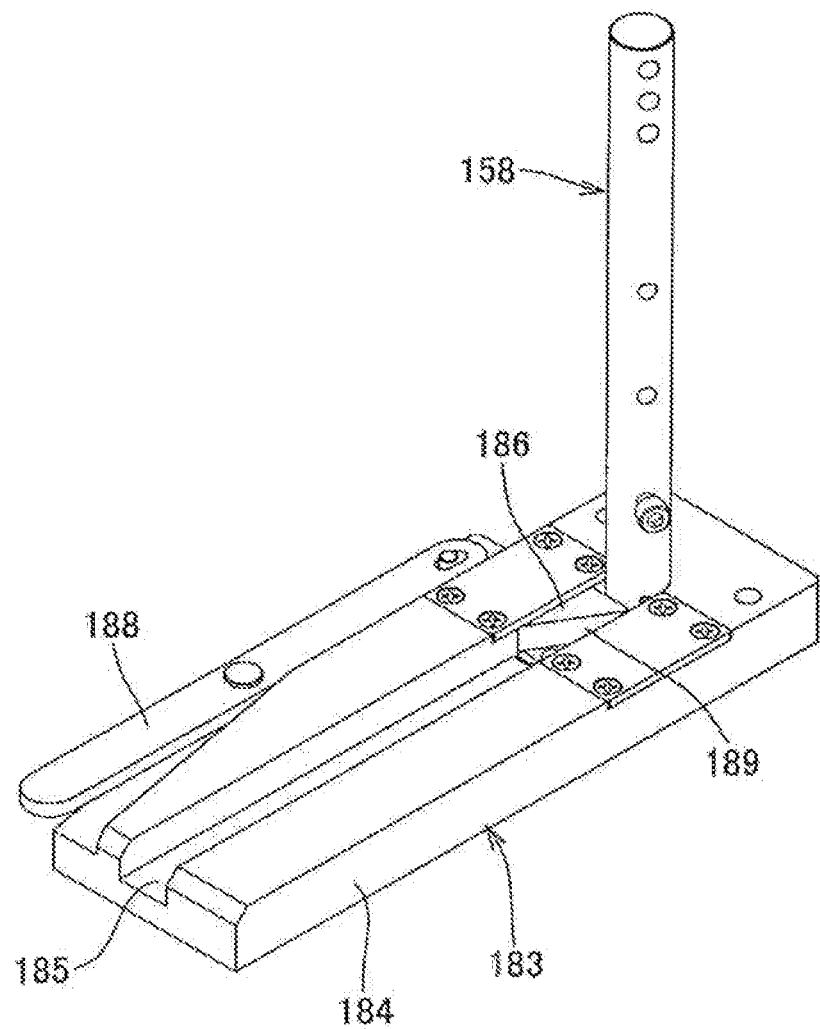
FIG. 27 is a perspective view of a guide unit which slidingly guides and rotatably supports the lower end of the rotary shaft body.
Figure 28:
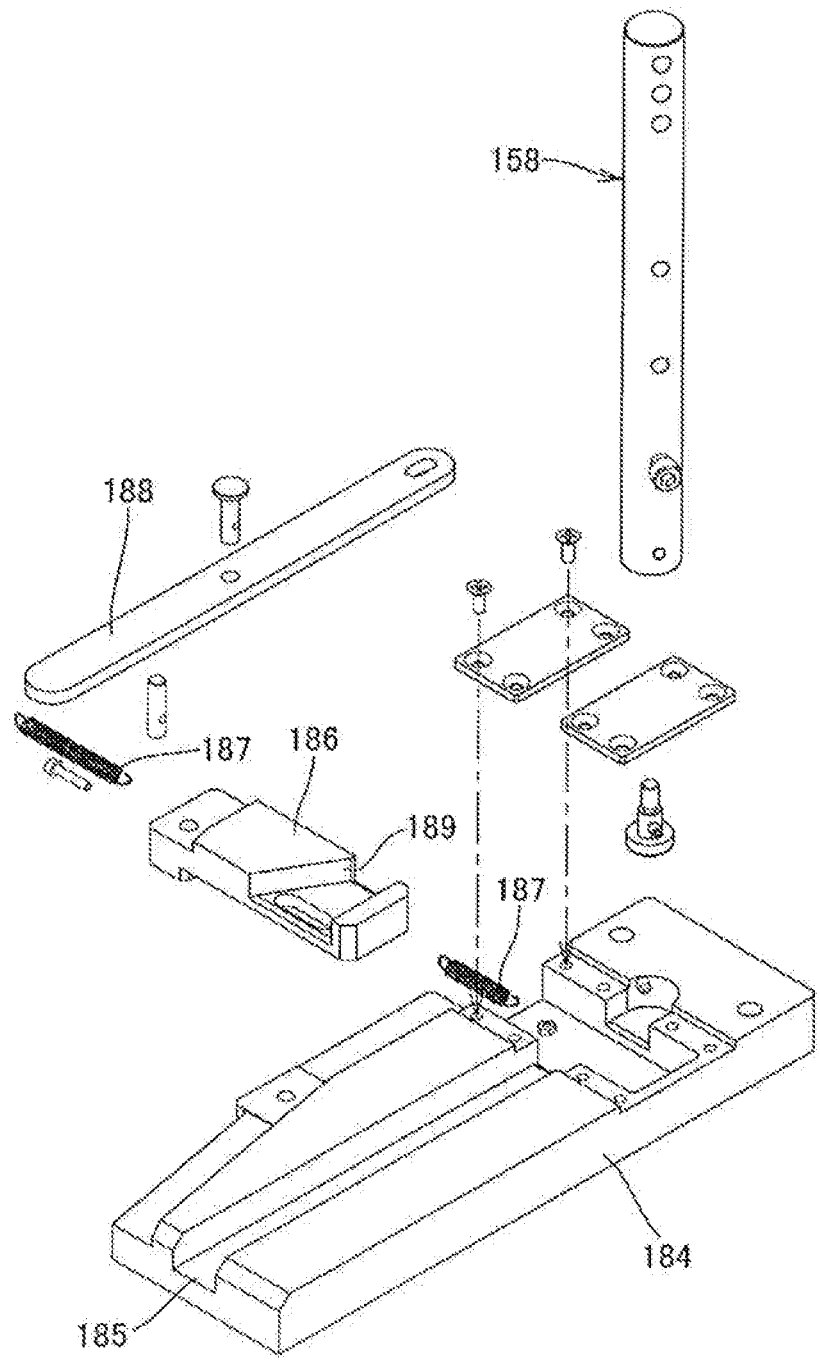
FIG. 28 is an exploded perspective view of the guide unit.

An opening/closing door 182 is provided on the front of the incubator chamber 101, the opening/closing door 182 is opened, and the rotary shaft 108 is divided at the connection unit 133, thereby making it possible to take the holder 110 located below the connection unit 133 out of the incubator chamber 101 as it is, and perform maintenance and cleaning thereon. The weight of the holder 110 is heavy because most of the components thereof are made of stainless steel. Therefore, in order to reduce the labor for introducing/removing the holder 110 into/from the incubator chamber 101, a guide unit 183 is provided on the bottom face of the incubator chamber 101 to slidingly guide the lower end part of the connection shaft 158, the lower end part projecting downward from the fixation disc 139, in the depth direction. The guide unit 183 also has a bearing function for rotatably supporting the lower end part of the connection shaft 158 during normal cell culture. Specifically, as illustrated in FIGS. 27 and 28, the guide unit 183 has the following structure. A guide groove 185 which slidingly guides the lower end part of the connection shaft 158 is formed on the upper face of a flat base 184 which extends in the depth direction of the incubator chamber 101 from the front end through the deep part thereof. A restriction member 186 is provided on the deep part of the guide groove 185 so as to pass across the guide groove 185 from the lateral side. The restriction member 186 is biased by a tension coil spring 187 so as to be movable. Further, a release lever 188 is provided along one side of the base 184, and the central part of the release lever 188 is axially supported on the base 184. Further, the rear end part of the release lever 188 is pivotally supported on one end part of the restriction member 186. An inclined claw portion 189 of the restriction member 186 is moved against the elastic biasing force of the tension coil spring 187 when the lower end part of the connection shaft 158 passes therethrough, and the inclined claw portion 189 returns to its original position after the connection shaft 158 passes therethrough so that the inclined claw portion 189 abuttingly locks and rotatably holds the connection shaft 158. When taking the holder 110 out of the incubator chamber 101, the front side of the release lever 188 is operated to displace the restriction member 186 to a release state, and the lower end part of the connection shaft 158 is thereby allowed to slide to the front side along the guide groove 185.

Further, a circulation type air cleaner 190 having a built-in high efficiency particulate air filter (HEPA filter) and a built-in fan is provided inside the incubator chamber 101, preferably, on the upper face thereof so that fine dust contained in the atmosphere inside the incubator chamber 101 can be removed. Further, $CO_2$ gas can be supplied into the incubator chamber 101 in order to improve the cell culture environment. The Petri dish 104 with the top lid 105 is also called a cell culture dish. In the cell culture apparatus of the present invention, it is assumed that the number of dishes to be used is eight to thirty-two in maximum (eight dishes per stage) in the case of a 60 mm dish and six to twenty-four in maximum (six dishes per stage) in the case of a 100 mm dish.

Figure 17:
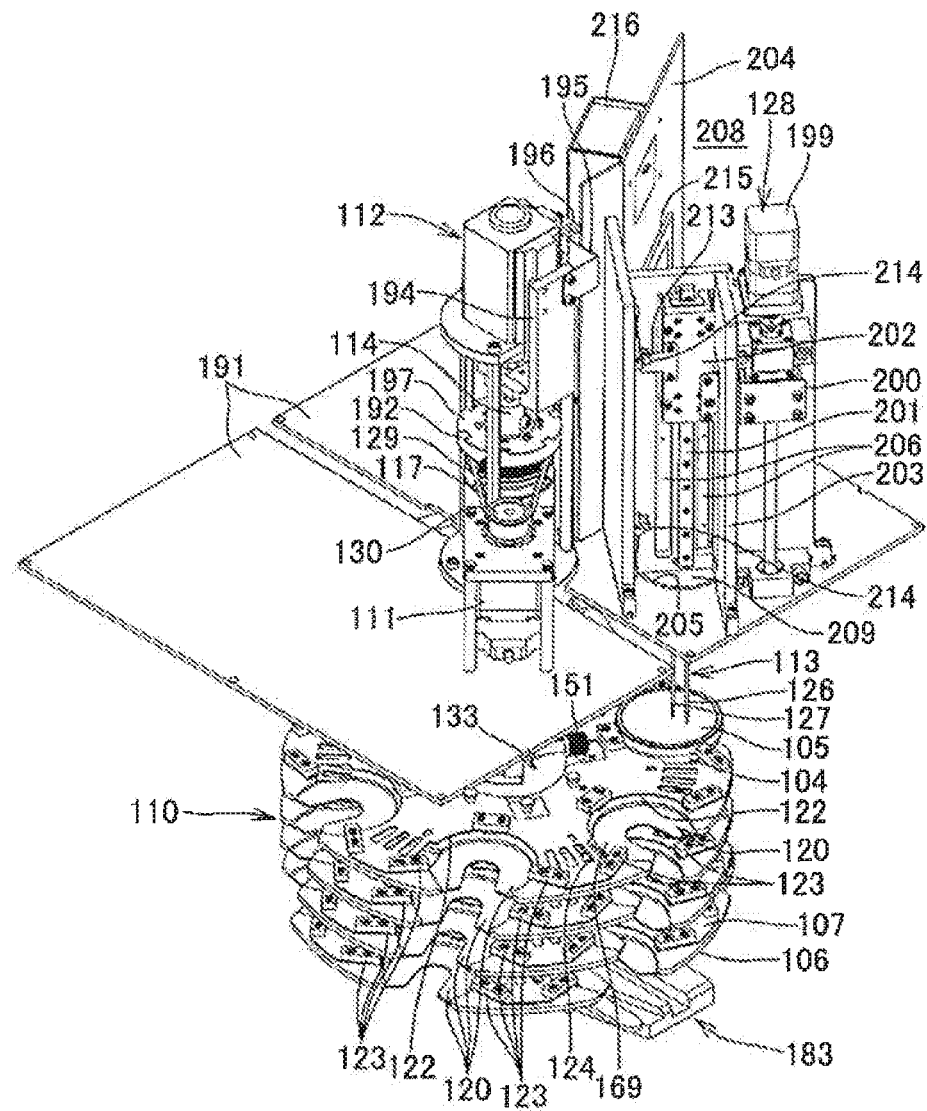
FIG. 17 is a partially-omitted perspective view of the cell culture apparatus of the second embodiment viewed from the upper side.
Figure 18:
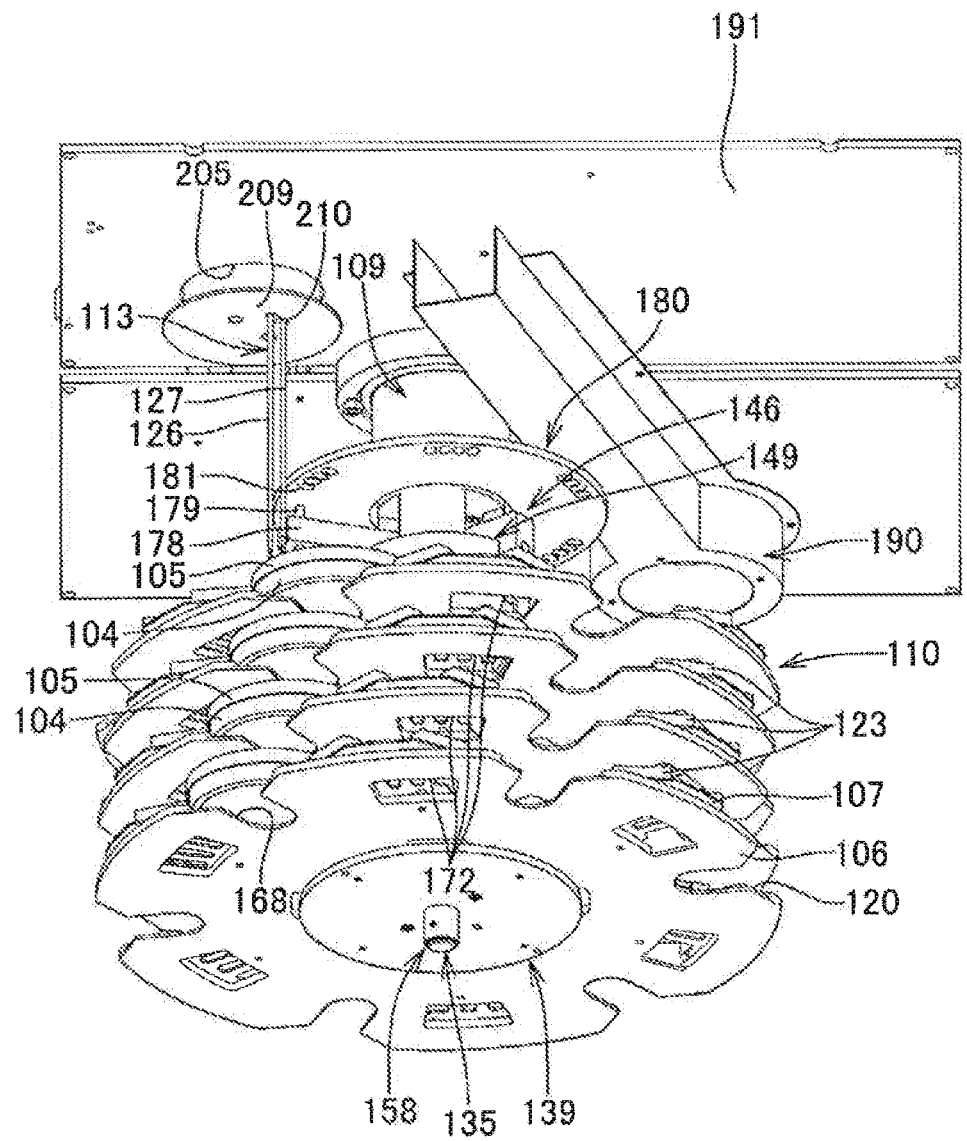
FIG. 18 is a partially-omitted perspective view of the cell culture apparatus of the second embodiment viewed from the lower side.
Figure 19:
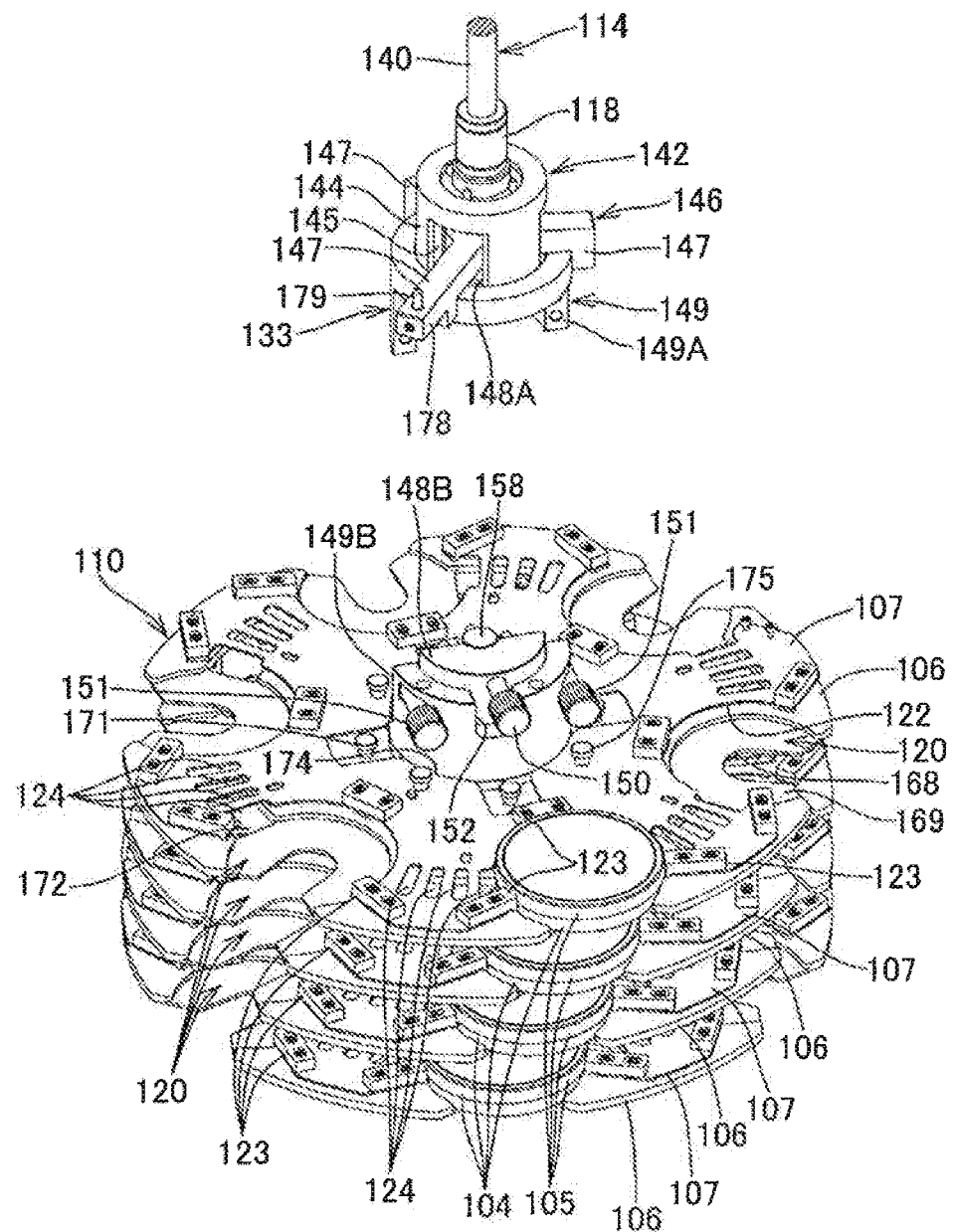
Figure 20:
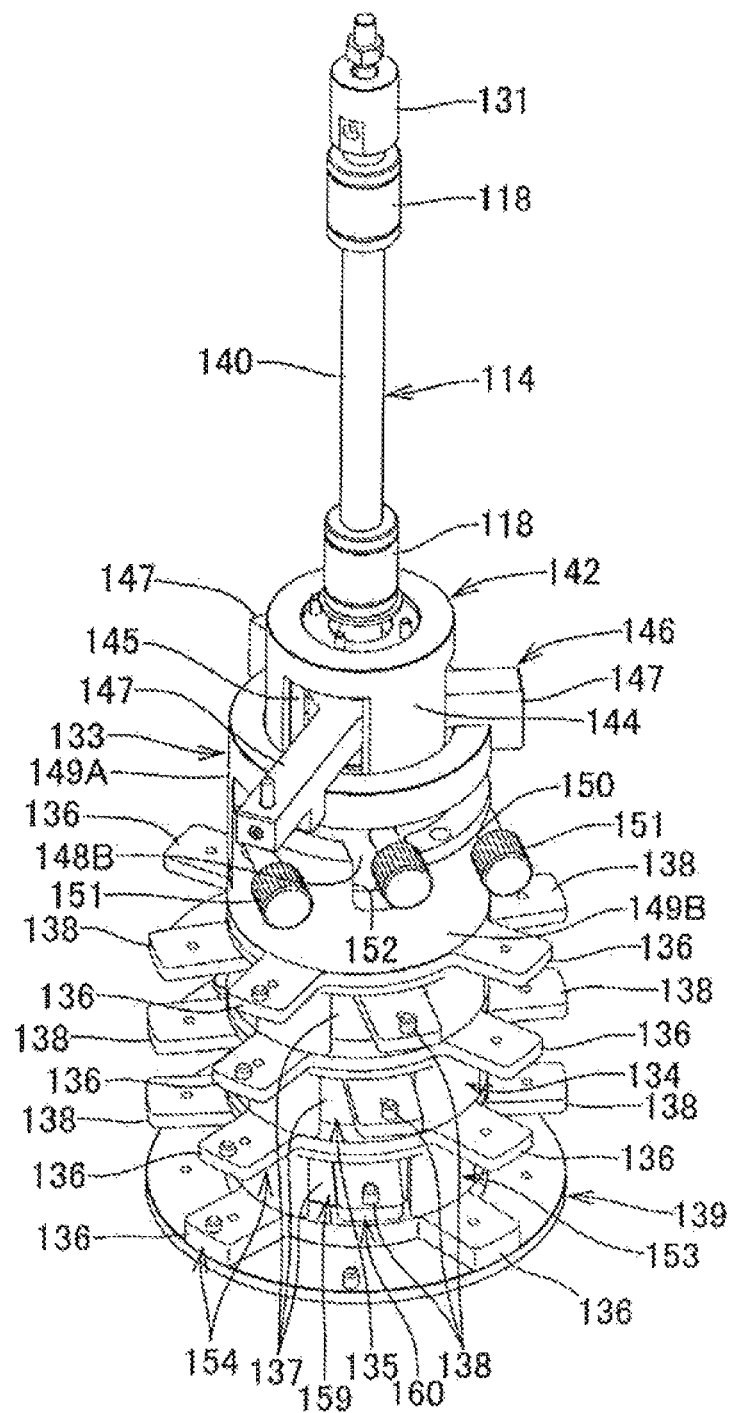
FIG. 20 is a perspective view illustrating the structure of the lower part of the rotary shaft body.
Figure 21:
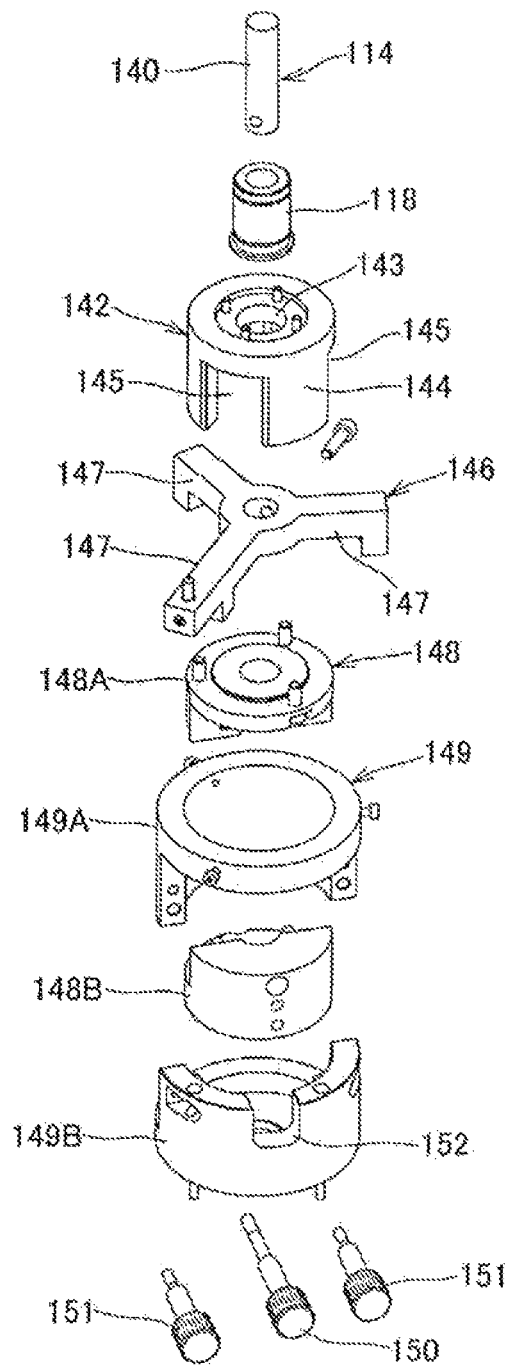
FIG. 21 is an exploded perspective view illustrating the structure of the connection unit of the rotary shaft body.
Figure 22:
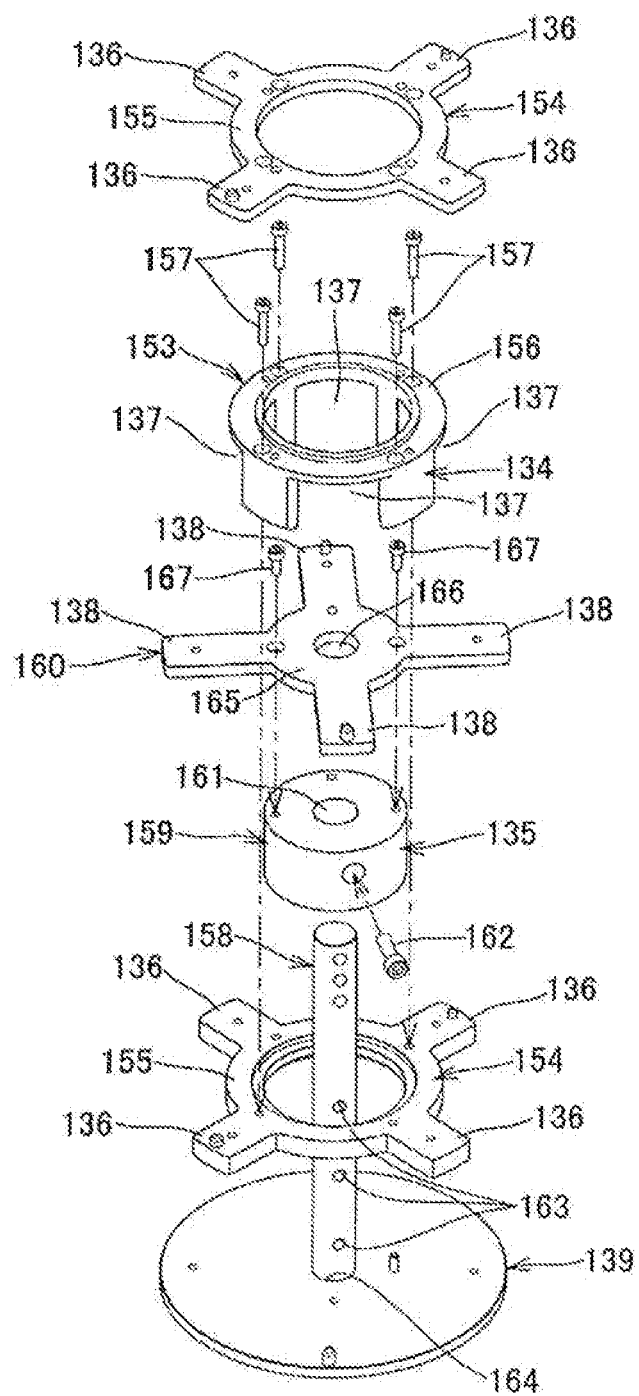
FIG. 22 is an exploded perspective view illustrating the structure of the lower part of the rotary shaft body.

Inside the drive chamber 102, there are stored drive units including the drive motor 111 which drives the second shaft body 115 to rotate, the linear actuator 112 which drives the first shaft body 114 to move up and down, and the liner actuator 128 which drives the culture medium replacement means 13 to move up and down. These mechanisms are provided on a base plate 191 which is disposed on the upper face of the partition wall 103 which forms the incubator chamber 101. In FIGS. 17 and 18, the partition wall 103 is omitted. In order to monitor the rotation position of the second shaft body 115, a disc 192 with a marker which is fixed to the upper end of the second shaft body 115 and an optical sensor 193 which optically reads the marker portion on the outer periphery of the disc 192 are provided in the fixed portion. Further, in order to monitor up-down termination positions of the first shaft body 114, the position of a movable piece 195 which is connected to the drive unit 132 of the linear actuator 112 and guided in the vertical direction by a linear guide 194 is confirmed using optical sensors 196, 196 arranged on the upper and lower sides or a limit switch to generate a signal for stopping the linear actuator 112. Further, it is also necessary to monitor the rotation position of the first shaft body 114. Therefore, a disc 197 with a marker is fixed to the upper end part of the first shaft body 114, and an optical sensor 198 which optically reads the marker portion on the outer periphery of the disc 197 is provided in the linear guide 194.

Figure 15:
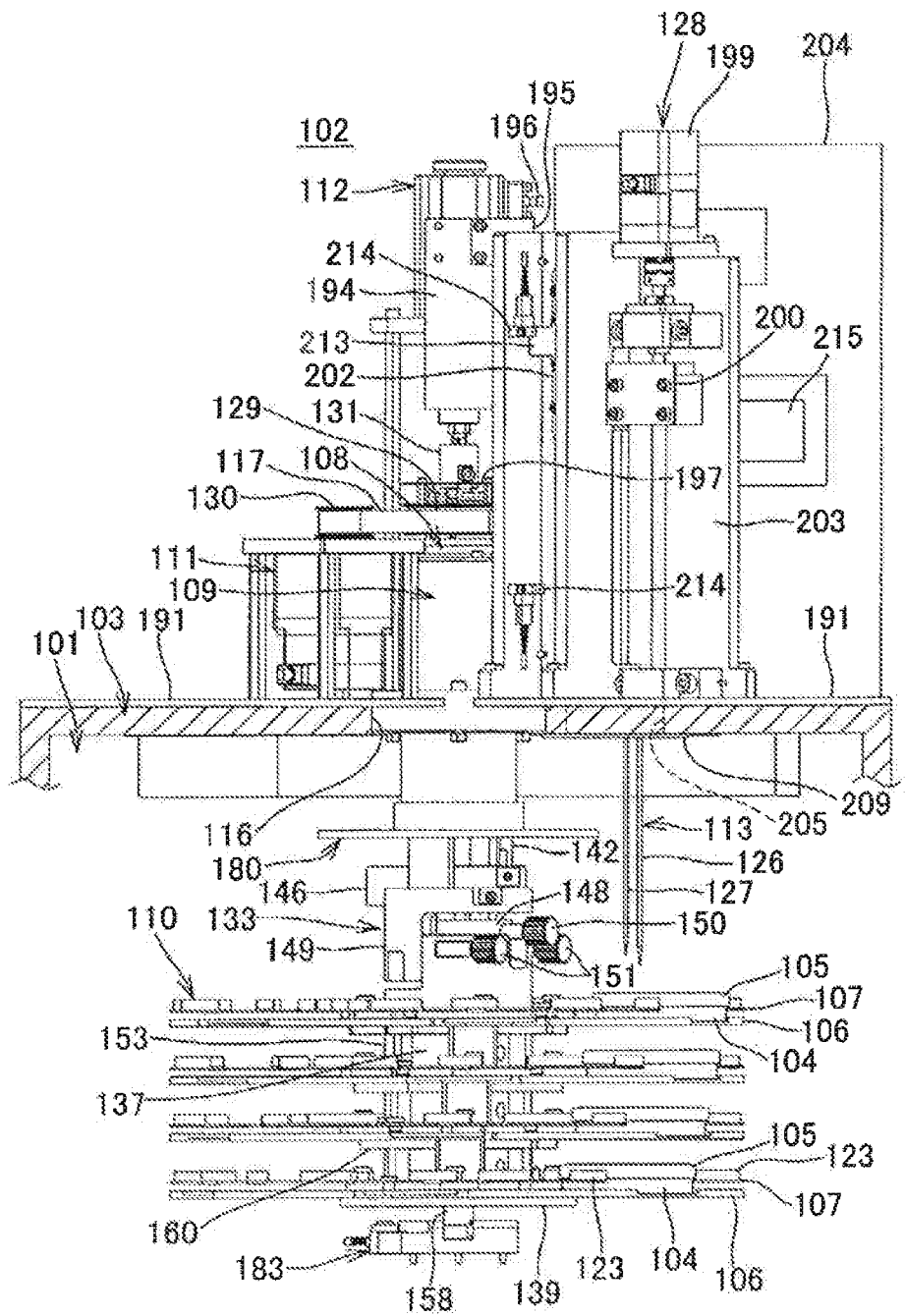
FIG. 15 is a schematic front view illustrating the internal structure of the cell culture apparatus of the second embodiment.
Figure 16:
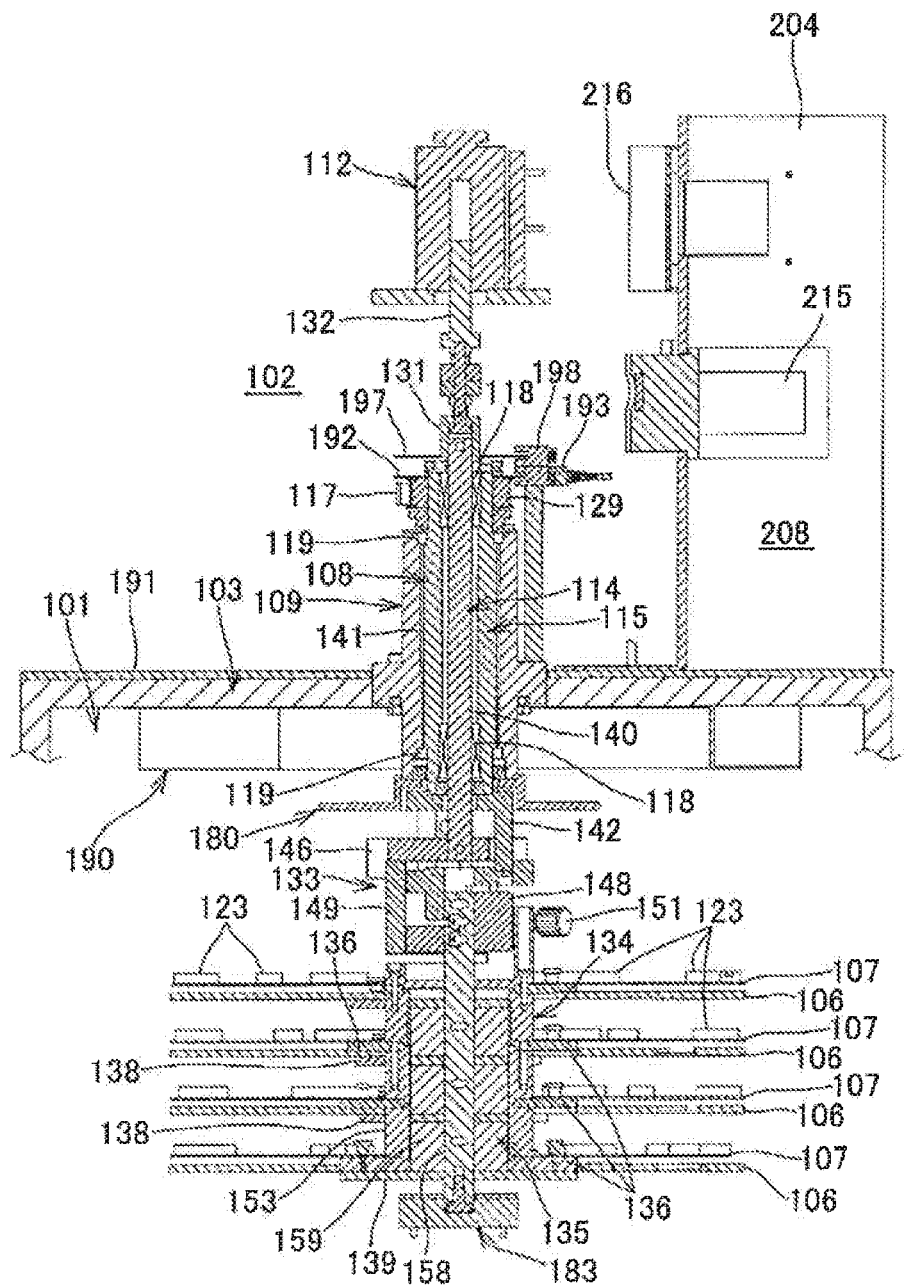
FIG. 16 is a longitudinal sectional front view of the cell culture apparatus of the second embodiment.

As illustrated in FIGS. 15 to 17, the linear actuator 128 which drives the culture medium replacement means 113 is placed on the base plate 191. Because the feed rate of the linear actuator 128 becomes large, there is employed a structure in which a movable unit 202 of a linear guide 201 which is vertically arranged is driven by a feed screw mechanism 200 which is driven by a stepping motor 199. These devices constituting the linear actuator 128 are attached to a fixation structure 203 which stands on the base plate 191, and a partition plate 204 which is formed in a bent shape is provided at a position at which the fixation structure 203 does not exist. Further, a through hole 205 is formed on the partition wall 103 and the base plate 191 both located under the linear guide 201, and the suction tube 126 and the ejection tube 127 are introduced into the incubator chamber 1 through the through hole 205. Further, a part of the movable unit 202 which is driven to move up and down by the linear actuator 128 provided in the drive chamber 102 is allowed to pass through an elongated slit 206 which is formed on the fixation structure 203 so as to face an operation space 208 which is partitioned by the fixation structure 203 and the partition plate 204 and an operation door 207 formed on the side face of a casing which faces the fixation structure 203 and the partition plate 204. The upper end parts of the suction tube 126 and the ejection tube 127 which are both vertically arranged inside the operation space 208 are held by the part of the movable unit 202. The movable piece 195 and the optical sensors 196 can be inspected through a gap between the fixation structure 203 and the partition plate 204.

Further, a guide hole 210 which guides the middle parts of the suction tube 126 and the ejection tube 127 is formed on an introduction member 209 which is provided in the through hole 205 on the partition wall 103. The lower end parts of the suction tube 126 and the ejection tube 127 inserted through the guide hole 210 are introduced into the Petri dish 104 by driving the linear actuator 128. Further, a suction pump 211 which is provided on the outer face of a side wall of the drive chamber 102 is connected to the suction tube 126, and an old culture medium is discharged into an external waste liquid tank (not illustrated). On the other hand, an ejection pump 212 which is also provided on the outer face of the side wall of the drive chamber 102 is connected to the ejection tube 127, and a new culture medium is supplied from an external culture medium tank. Independent peristaltic pumps are used as the suction pump 211 and the ejection pump 212. Further, a gas seal for improving the air-tightness is provided between the suction tube 126 and the ejection tube 127 and the guide hole 210. In order to accurately control the height positions of the lower ends of the suction tube 126 and the ejection tube 127, the position of a movable piece 213 which is fixed to the movable unit 202 is detected by optical sensors 214, 214 which are attached to the fixation structure 203 or a limit switch. The suction tube 126 and the ejection tube 127 can each be replaced inside the operation space 208. Further, the partition plate 204 inside the operation space 208 is provided with a control panel 215 so that basic setting can be performed. Further, drivers 216 which control various motors are attached to the back face of the partition plate 204. The cell culture apparatus of the present invention can be controlled in detail by a personal computer.

In the cell culture apparatus of the present invention having the above configuration, the lower disc 106 which holds the Petri dishes 104 and the upper disc 107 which holds the top lids 5 of the Petri dishes 104 are defined as one set, and two or more sets are vertically arranged in multiple stages. The lower disc 106 on each of the stages is directly or indirectly fixed to the lower part of the second shaft body 115. The upper disc 107 on each of the stages is directly or indirectly fixed to the lower part of the first shaft body 114. All the lower discs 106 on the respective stages are integrally driven to rotate by the synchronous rotation means functioning by the second shaft body 115. All the upper discs 107 on the respective stages are integrally driven to move up and down by the first shaft body 114. For example, when the upper discs 107 are moved upward, the rotation restriction means functions to stop the upper discs 107 and the lower discs 106 are driven to rotate by a predetermined rotation angle to thereby laterally shift the top lids 105 so that the Petri dishes 104 are partially exposed. The Petri dishes 104 and the top lids 105 held on the respective stages are held at positions displaced by a certain angle in one rotation direction from the highest stage to the lowest stage so that all of the Petri dishes 104 are set to be partially exposed in plan view when shifting the top lids 105 therefrom. In addition, the insertion holes 124 are formed on the upper disc 107 on each of the stages at positions corresponding to the exposed portions of the Petri dishes 104 located below. The through holes 172 are formed on at least the lower discs 106 on the respective stages excepting the lowest stage at positions corresponding to the exposed portions of the Petri dishes 104 located on the lower stage. The culture medium replacement means 113 is inserted into the Petri dish 104 on the highest stage through the insertion hole 124 of the upper disc 107 on the highest stage to thereby replace the culture medium. The culture medium replacement means 113 is inserted into the Petri dish 104 on each of the other lower stages through the insertion holes 124 of the respective upper discs 107 and the through holes 172 of the respective lower discs 106 located thereabove to thereby replace the culture medium. Various modifications that can maintain the above basic structure fall within the scope of the present invention.

REFERENCE SIGNS LIST

1 Incubator chamber
2 Drive chamber
3 Partition wall
3A Through hole
4 Petri dish
5 Top lid
6 Upper Petri dish
7 Top lid
8 Rotary shaft body
9 Bearing unit
10 Holder
11 Drive motor
12 Linear actuator
13 Culture medium replacement means
14 Rotary cylinder (first shaft body)
15 Center shaft (second shaft body)
16 Shaft hole
17 Timing belt
18 Lower-stage lower disc (lower disc)
19 Lower-stage upper disc (upper disc)
20 Holding unit
21 Projection
22 Opening
23 Top lid holding unit
24 Insertion hole
25 Locking claw
26 Suction tube
27 Ejection tube
28 Linear actuator
29 Upper-stage lower disc
30 Upper-stage upper disc
31 Connection rod
32 Escape hole
33 Second holding unit
34 Projection
35 Opening
36 Top lid holding unit
37 Insertion hole
38 Locking claw
39 Through hole
40 Support rod 41 Flange plate
42 Suction pump
43 Ejection pump
44 Guide groove
44A Vertical portion (synchronous rotation means)
44B Horizontal portion
45 Pin (synchronous rotation means)
46 Opening/closing door
47, 48, 49, 50 Cutout portion
101 Incubator chamber
102 Drive chamber
103 Partition wall
104 Petri dish
105 Top lid
106 Lower disc
107 Upper disc
108 Rotary shaft body
109 Bearing unit
110 Holder
111 Drive motor
112 Linear actuator
113 Culture medium replacement means
114 First shaft body
115 Second shaft body
116 Shaft hole
117 Timing belt
118 Bush
119 Bearing
120 Holding unit
122 Opening
123 Top lid holding unit
124 Insertion hole
125 Cutout portion
126 Suction tube
127 Ejection tube
128 Linear actuator
129 Pulley
130 Pulley
131 Rotary joint
132 Drive unit
133 Connection unit
134 Outer shaft portion
135 Inner shaft portion
136 Fixation piece
137 Opening portion
138 Fixation piece
139 Fixation disc
140 Center shaft
141 Drive shaft
142 Outer-inner conversion member
143 Circular hole
144 Cylindrical portion
145 Opening
146 Inner-outer conversion member
147 Connection piece
148 Inner connection member
148A Upper portion
148B Lower portion
149 Outer connection member
149A Upper portion
149B Lower portion
150 Connection screw
151 Connection screw
152 Cutout
153 Spacer cylinder
154 Upper fixation member
155 Ring portion
156 Engagement step portion
157 Fixation screw
158 Connection shaft
159 Spacer shaft
160 Lower fixation member
161 Insertion hole
162 Fixation screw
163 Engagement hole
164 Center hole
165 Center disc
166 Center hole
167 Fixation screw
168 Cutout portion
169 Recessed step portion
170 Attachment opening
171 Fastening screw
172 Through hole
173 Locking claw
174 Attachment opening
175 Fastening screw
176 Pin (synchronous rotation means)
177 Engagement hole (synchronous rotation means)
178 Extended portion
179 Pin (rotation control means)
180 Control plate
181 Engagement hole (rotation restriction means)
182 Opening/closing door
183 Guide unit
184 Base
185 Guide groove
186 Restriction member
187 Tension coil spring
188 Release lever
189 Inclined claw portion
190 Air cleaner
191 Base plate
192 Disc
193 Optical sensor
194 Linear guide
195 Movable piece
196 Optical sensor
197 Disc
198 Optical sensor
199 Stepping motor
200 Screw mechanism
201 Linear guide
202 Movable unit
203 Fixation structure
204 Partition plate
205 Through hole
206 Elongated slit
207 Operation door
208 Operation space
209 Introduction member
210 Guide hole
211 Suction pump
212 Ejection pump
213 Movable piece
214 Optical sensor
215 Control panel
216 Drivers

The invention claimed is:
1. A cell culture apparatus having a culture medium replacement function, wherein
at least one set of upper and lower discs each fixed to a rotatable shaft is horizontally arranged inside an incubator chamber, Petri dishes in each of which cells and a culture medium are put are held on the lower disc, top lids are held on the upper disc, a lower side of each of the top lids is open, it is possible to achieve a state in which the lower disc and the upper disc are brought vertically close to each other to cover the Petri dishes with the top lids and a state in which the lower disc and the upper disc are vertically separated from each other and one of the lower disc and the upper disc is rotated by a predetermined angle to laterally shift the top lids from the Petri dishes so that the Petri dishes are partially exposed, culture medium replacement means is inserted into the exposed portion of a Petri dish from the upper side through a first insertion hole of a plurality of insertion holes formed on the upper disc, and the culture medium is replaced, the culture medium replacement means is then retracted, and the lower disc and the upper disc are rotated and vertically displaced to cover the Petri dishes with the top lids to continue cell culture, wherein the plurality of insertion holes are formed to penetrate the upper disc, each of the plurality of holes being located at a position near to a corresponding one of the top lids.

2. The cell culture apparatus having a culture medium replacement function according to claim 1, wherein
an incubator chamber and a drive chamber located above the incubator chamber are arranged with a partition wall interposed therebetween,
a rotary shaft body includes a first shaft body and a second shaft body which both have the same rotation center and are coaxially arranged wherein the first shaft body is slidable in the axial direction relative to the second shaft body and the first shaft body and the second shaft body are relatively rotatable by a predetermined angle, the rotary shaft body being allowed to vertically pass through a shaft hole formed on the partition wall and supported by a bearing unit,
the second shaft body of the rotary shaft body is supported so as to be rotatable at a fixed position and driven to rotate by a motor arranged inside the drive chamber, and the first shaft body of the rotary shaft body is driven to move up and down in the vertical direction by a linear actuator arranged inside the drive chamber,
the lower disc which holds Petri dishes is directly or indirectly concentrically fixed to a lower part of the second shaft body and an upper disc which holds top lids of the Petri dishes is directly or indirectly concentrically fixed to a lower part of the first shaft body inside the incubator chamber,
a plurality of holding units which mount thereon and hold the Petri dishes are provided in the lower disc on the same circumference at every constant rotation angle,
a plurality of openings which receive the Petri dishes are formed on the upper disc so that the center of each of the openings is located at the same position as the center of the corresponding holding unit, top lid holding units which hold outer peripheral parts of the top lids of the Petri dishes are provided on peripheral edges of the openings, and insertion holes are formed to penetrate the upper disc at positions close to one side of top lids held on the top lid holding units,
a suction tube and an ejection tube for sucking and ejecting a culture medium and constituting the culture medium replacement means are allowed to penetrate the partition wall so as to hang down to the incubator chamber and driven to move up and down by a linear actuator provided inside the drive chamber, and
cells are cultured in a state in which the upper disc is moved down with the relative rotation angle between the upper disc and the lower disc maintained zero to cover the Petri dishes with the top lids, the upper disc is then moved up and the lower disc is rotationally displaced by a predetermined angle relative to the upper disc to shift the top lids from the Petri dishes, the suction tube and the ejection tube are moved down so that tips of the suction tube and the ejection tube are located inside a Petri dish through the corresponding insertion hole of the upper disc, an old culture medium is discharged using the suction tube, and a new culture medium is then injected from the ejection tube to automatically replace the culture medium.

3. The cell culture apparatus having a culture medium replacement function according to claim 2, wherein two or more sets, each of the sets including a lower disc which holds Petri dishes and an upper disc which holds top lids of the Petri dishes, are vertically arranged in multiple stages, a lower disc on each of the stages is directly or indirectly fixed to the lower part of the second shaft body, an upper disc on each of the stages is directly or indirectly fixed to the lower part of the first shaft body, all lower discs on the respective stages are integrally driven to rotate by the second shaft body, all upper discs on the respective stages are integrally driven to move up and down by the first shaft body, Petri dishes and top lids held on the respective stages are held at positions displaced by a predetermined angle in one rotation direction from the highest stage to the lowest stage so that all the Petri dishes are set to be partially exposed in plan view when shifting the top lids therefrom, the insertion holes are formed on the upper disc on each of the stages at positions corresponding to the exposed portions of the Petri dishes located below, through holes are formed on at least lower discs on the respective stages excepting the lowest stage at positions corresponding to the exposed portions of Petri dishes located on the lower stage, the culture medium replacement means is inserted into a Petri dish on the highest stage through the corresponding insertion hole of the upper disc on the highest stage to replace the culture medium, and the culture medium replacement means is inserted into a Petri dish on each of the other lower stages through the insertion holes of the respective upper discs and the through holes of the respective lower discs located thereabove to replace the culture medium.

4. The cell culture apparatus having a culture medium replacement function according to claim 2, further comprising synchronous rotation means which functions in a state in which the upper disc is moved down with the relative rotation angle between the upper disc and the lower disc maintained zero to cover Petri dishes with top lids and integrates the upper disc and the lower disc with each other with respect to rotation and rotation restriction means which functions in a state in which the upper disc is moved upward to remove top lids from Petri dishes and prevents rotation of the upper disc.

5. The cell culture apparatus having a culture medium replacement function according to claim 2, wherein a lower part of the rotary shaft body located inside the incubator chamber includes a cylindrical outer shaft portion composed of one of the first shaft body and the second shaft body and an inner shaft portion located inside the outer shaft portion and composed of the other one of the first shaft body and the second shaft body, one of the upper disc and the lower disc is fixed to a plurality of fixation pieces which are provided in a projecting manner on the outer periphery of the outer shaft portion, the other one of the upper disc and the lower disc is fixed to a plurality of fixation pieces which are provided in a projecting manner on the outer periphery of the inner shaft portion and project outward in the radial direction through a plurality of opening portions formed on the outer shaft portion, and the opening portions have a size that allows the fixation pieces of the inner shaft portion to relatively move upward and displace by a predetermined angle inside thereof at the time of an operation for opening the top lids.

6. The cell culture apparatus having a culture medium replacement function according to claim 2, wherein the rotary shaft body located inside the incubator chamber includes a connection unit which is located above the upper disc on the highest stage and capable of vertically separating and connecting the first shaft body and the second shaft body.

7. The cell culture apparatus having a culture medium replacement function according to claim 2, wherein a through hole through which the suction tube and the ejection tube are introduced into the incubator chamber is formed on the partition wall, a support rod which is driven to move up and down by a linear actuator provided in the drive chamber is vertically arranged so as to pass through the through hole, the suction tube and the ejection tube is allowed to penetrate a flange plate which is fixed to a lower end of the support rod and located inside the incubator chamber and fixed thereto, the through hole is air-tightly closed by the flange plate when the support rod is moved upward, and the support rod is moved downward to introduce the tips of the suction tube and the ejection tube into the Petri dish.

8. The cell culture apparatus having a culture medium replacement function according to claim 2, wherein the bearing unit which rotatably supports the rotary shaft body on the partition wall and the rotary shaft body each include a gas seal function for maintaining the incubator chamber in an air-tight state.

9. The cell culture apparatus having a culture medium replacement function according to claim 2, wherein an opening/closing door is provided on the front of the incubator chamber, cutout portions are formed so that, when the positions of the holding units of the lower disc and the positions of the top lid holding units of the upper disc are vertically aligned to each other, fingers can pass from the outer peripheral parts through the holding units and the top lid holding units, and the cutout portions of the upper disc are allowed to communicate with the openings.

10. The cell culture apparatus having a culture medium replacement function according to claim 2, wherein each of the holding units of the lower disc is a recessed step portion which is formed on the upper face of a surrounding area of the corresponding cutout portion and receives a bottom part of a Petri dish.

11. The cell culture apparatus having a culture medium replacement function according to claim 2, wherein each of the top lid holding units of the upper disc abuttingly locks the outer peripheral face of a top lid of a Petri dish and includes three or more locking claws which support the lower edge of the top lid and are arranged on a peripheral edge part of the corresponding opening.

* * * * *